United States Patent
Dick et al.

(10) Patent No.: US 7,909,463 B2
(45) Date of Patent: *Mar. 22, 2011

(54) METHOD FOR DETERMINING VISION DEFECTS AND FOR COLLECTING DATA FOR CORRECTING VISION DEFECTS OF THE EYE BY INTERACTION OF A PATIENT WITH AN EXAMINER AND APPARATUS THEREFOR

(75) Inventors: Manfred Dick, Gefell (DE); Holger Mäusezahl, Jena (DE); Eckhard Schröder, Eckental (DE)

(73) Assignee: Carl Zeiss Meditec AG, Jena (DE)

( * ) Notice: Subject to any disclaimer, the term of this patent is extended or adjusted under 35 U.S.C. 154(b) by 204 days.

This patent is subject to a terminal disclaimer.

(21) Appl. No.: 11/924,294

(22) Filed: Oct. 25, 2007

(65) Prior Publication Data

US 2008/0100803 A1    May 1, 2008

Related U.S. Application Data

(63) Continuation-in-part of application No. PCT/EP2007/000388, filed on Jan. 17, 2007.

(51) Int. Cl.
*A61B 3/10* (2006.01)
*A61B 3/14* (2006.01)
*A61B 3/00* (2006.01)

(52) U.S. Cl. ......... 351/211; 351/212; 351/206; 351/246
(58) Field of Classification Search .......... 351/205–206, 351/211–212, 246
See application file for complete search history.

(56) References Cited

U.S. PATENT DOCUMENTS

| | | | |
|---|---|---|---|
| 4,579,430 A | 4/1986 | Bille | |
| 5,142,132 A | 8/1992 | MacDonald et al. | |
| 5,675,399 A | 10/1997 | Kohayakawa | |
| 5,805,119 A | 9/1998 | Erskine et al. | |
| 6,116,736 A * | 9/2000 | Stark et al. | 351/206 |
| 7,338,165 B2 | 3/2008 | Dai | |
| 2003/0048413 A1* | 3/2003 | Ross et al. | 351/211 |
| 2004/0100619 A1 | 5/2004 | Olivier et al. | |
| 2005/0010115 A1* | 1/2005 | Bone et al. | 600/476 |
| 2008/0018855 A1 | 1/2008 | Larichev et al. | |

FOREIGN PATENT DOCUMENTS

| | | |
|---|---|---|
| DE | 37 33 872 A1 | 6/1988 |
| DE | 11 2005 000650 T5 | 3/2007 |
| WO | WO 93 22711 | 11/1993 |
| WO | WO 2005/089635 A | 9/2005 |

* cited by examiner

*Primary Examiner* — Darryl J Collins
*Assistant Examiner* — Zachary Wilkes
(74) *Attorney, Agent, or Firm* — Nils H. Ljungman & Associates

(57) ABSTRACT

Apparatus for determining defects of the retina of the eye by interaction between a patient and an examiner, which apparatus comprises an electronically-controlled, adaptive optical system configured to form an image in the eye of the patient.

20 Claims, 16 Drawing Sheets

FIG. 11 MICROMIRROR DEVICE
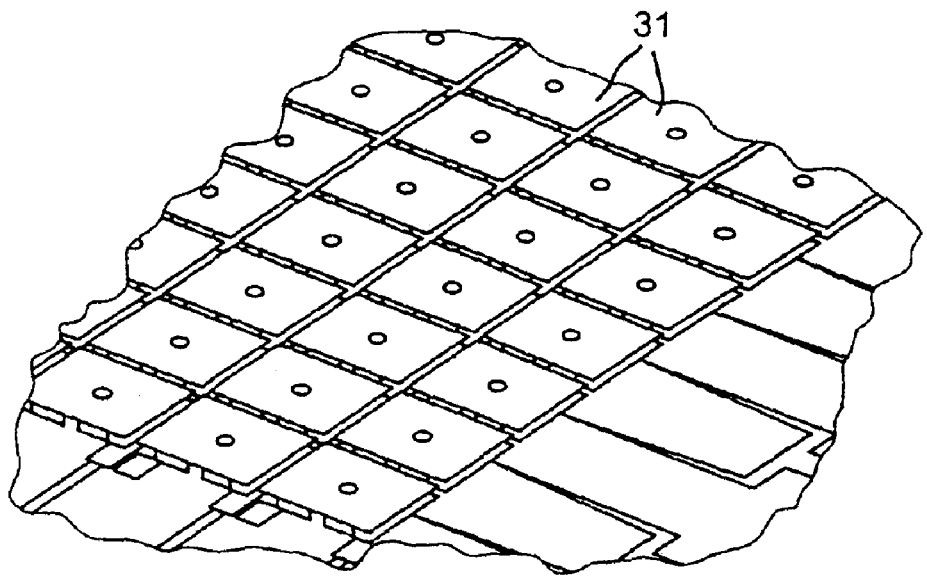
FIG. 12
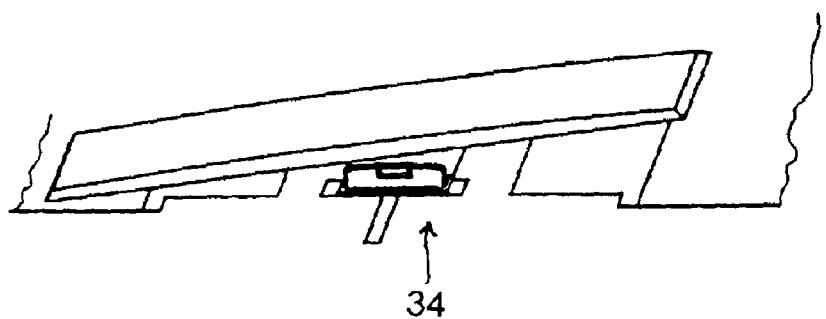
INTERFACE
ELECTROSTATIC
PIEZOELECTRIC
BIMORPH
ACTUATION

METHOD FOR DETERMINING VISION DEFECTS AND FOR COLLECTING DATA FOR CORRECTING VISION DEFECTS OF THE EYE BY INTERACTION OF A PATIENT WITH AN EXAMINER AND APPARATUS THEREFOR

CONTINUING APPLICATION DATA

This application is a Continuation-in-Part of International Application PCT/EP2007/000388 filed Jan. 17, 2007, which claims priority from pending U.S. application Ser. No. 11/333,757, which is a Continuation-in-Part of U.S. application Ser. No. 10/827,463, filed Apr. 19, 2004, now issued as U.S. Pat. No. 6,997,555 on Feb. 14, 2006, which is a continuation of U.S. application Ser. No. 10/160,345, filed May 31, 2002, now issued as U.S. Pat. No. 6,722,767 on Apr. 20, 2004. International Application No. PCT/EP2007/000388 was pending as of the filing date of the present application. International Application No. PCT/EP2007/000388 claims priority from U.S. application Ser. No. 11/333,757. U.S. application Ser. No. 10/160,345 was a Continuation-in-Part application of International Application No. PCT/EP00/12116, filed on Dec. 1, 2000, and claiming priority from Federal Republic of Germany Patent Application No. DE 199 58 436.2, filed on Dec. 3, 1999. International Application No. PCT/EP00/12116 was pending as of the filing date of U.S. application Ser. No. 10/160,345. The United States was an elected state in International Application No. PCT/EP00/12116.

BACKGROUND

1. Technical Field

This application relates in one aspect to a method for determining vision defects and for collecting data for correcting vision defects of the eye by interaction of a patient with an examiner and apparatus therefor.

2. Background Information

The primary or traditional method for correcting vision defects, such as, correcting myopia, hyperopia, and astigmatism, comprises selection of and mounting of particular lenses in a spectacle-frame by the physician for a vision test, and the patient establishes his optimal faculty of vision based on the gradation of the test lines of a test image. In accordance with this traditional method, the patient can obtain optimally suited glasses for correction of significant, or approximate or gross, vision defects, but the method substantially may provide only for approximate or rough correction of vision defects.

This classical approach or method has now been replaced by objective metrological methods which are performed without active participation by the patient. Examples include automatic refractometers.

Next to the objective determination of significant vision defects, various topographical apparatus and devices for measuring eye aberrations, such as, aberroscopes or aberrometers, are utilized so as to determine patient-specific cornea topographies and, as well, substantially all wavefront aberrations. On the basis of such metrological data, the patients are treated, for example, by using an excimer laser system, to have specific topographies applied or formed on the cornea of the eye, which topographies are to ensure an optimal faculty of vision (compare: P. Mierdel, H.-E. Krinke, W. Wiegand, M. Kaemmerer, T. Seiler, "*Meβplatz zur Bestimmung der monochromatischen Aberration des menschlichen Auges {Test station for the determination of the monochromatic aberration of the human eye}* ", OPHTHALMOLOGE, 1997, 94; pages 441-445, SPRINGER VERLAG, 1997).

In these determinations, or measurements or metrological approaches, a double-pass through the optics system of the eye needs to be realized due to technical reasons. The main problem with this method resides therein that the uneven or odd-valent aberrations are determined in a falsified manner. A reduction of the problem with the double-pass method can be obtained, for example, by use of different numerical apertures for the entering and exiting light. Another approach comprises inducing of a fluorescence on the cornea so as to preclude these metrological errors (compare: LASER FOCUS WORLD, April 1999, pages 35-36).

In the methods available in the state of the art, an optical apparatus or system, the eye, which is a rather dynamic system, is precisely measured and corrected, but only in a momentary or snapshot-like manner. This suggests errors, particularly in the desired correction of higher-order aberrations which preclude attainment of an optimal faculty of vision. This is indicated thereby that with the measurements of eye aberrations of eyes actually having the best faculty of vision, occasionally high aberrations are shown, and till this day it is not known with certainty whether a physical correction of the eye actually increases or even worsens the faculty of vision of the eye.

It is further known that aberrations of the human eye can be compensated with the aid of adaptive optics, so as to realize high-resolution images of the cornea for medical investigations (compare: LASER FOCUS WORLD, August 1998, pages 18-22).

A microscope with an adaptive optics is described in German patent publication No. 19 733 193 A1. This publication mentions various wave modulators.

In the paper "*Supernormal vision and high-resolution retinal imaging through adaptive optics*," by Liang et al., J. Opt. Soc. Am. A, Vol. 14 (1997), pages 2884-2892, apparatus and method are described with which by way of a wavefront measurement, using a deformable mirror, the feasibility of an adaptive correction of eye aberrations as well as photographic images of the retina is achieved.

U.S. Pat. No. 5,777,719, which is incorporated by reference herein, issued to inventors Williams et al. on Jul. 7, 1998 and entitled "Method and apparatus for improving vision and the resolution of retinal images," also describes a method and a device for obtaining improved photographic pictures of the retina, with the apparatus, using a deformable mirror, being capable of obtaining corrected pictures of the retina using a CCD-camera. At the time of the Williams invention, despite significant advances in spectacle and contact lens design, ophthalmic lenses only corrected defocus and astigmatism. Spectacles and contact lenses left uncorrected additional aberrations such as spherical aberration, coma, and a host of irregular aberrations. These high order aberrations of the eye not only blur images formed on the retina, which impairs vision, but also blur images taken of the living human retina.

Subjective refractive methods of optometrists and objective autorefractors measure defocus and astigmatism only. They cannot measure the complete wave aberration of the eye, which includes all aberrations left uncorrected by conventional spectacles. The objective aberroscope disclosed by Walsh et al. in the Journal of the Optical Society of America A, Vol. 1, pp. 987-992 (1984) provides simultaneous wave aberration measurements of the entire pupil but cannot sample the pupil with a spacing finer than about 0.9 mm (See Charman in Optometry and Vision Science, Vol. 68, pp. 574-583 (1991)). Moreover, rapid, automated computation of the wave aberration has not been demonstrated with this method.

According to Williams, a Hartmann-Shack wavefront sensor can be used in to measure the wave aberrations of the human eye by sensing the wavefront emerging from the eye produced by the retinal reflection of a focused light beam on the fovea. The wavefront sensor can be used in cooperation with an adaptive optics arrangement comprising a deformable mirror, a device that has successfully compensated for atmospheric turbulence in ground-based telescopes. Williams combined these two systems to develop a method of and an apparatus for producing ophthalmic optical elements that provide improved or supernormal vision, as well as high resolution retinal images, specifically for accurately measuring higher order aberrations of the eye and for using the data thus measured to compensate for those aberrations with a customized optical element.

In the system of Williams, the wavefront in the plane of the pupil is recreated in the plane of a lenslet array of a Hartmann-Shack wavefront sensor. Each of the lenslets in the lenslet array is used to form an aerial image of the retinal point source on a CCD camera located adjacent to the lenslet array. The wave aberration of the eye, in the form of a point source produced on the retina by a laser beam, displaces each spot by an amount proportional to the local slope of the wavefront at each of the lenslets. The output from the digital CCD camera is sent to a computer which then calculates the wave aberration and provides a signal to a deformable mirror. The deformable mirror is modified until it ultimately acquires a shape that is identical to the wave aberration measured at the outset, but with half the amplitude. This deformation is the appropriate one to flatten the distorted wavefront into a plane wave, which improves image quality.

When the reconstructed wave aberration signal reaches a predetermined value based on computer calculations, the final aberration signal can be used to produce contact lenses to correct for all of the monochromatic aberrations of the human eye or for surgical procedures.

Williams' system can also be used to provide high resolution images of the retina. The system for producing such images uses a krypton flash lamp which is designed to illuminate a retinal disk to provide an image of the retina which is reflected by the deformable mirror onto a lens and through an aperture such that the reflected image of the retina is focused onto a second CCD camera. The signals generated by the camera are acquired in a manner similar to that described above in connection with the first CCD camera and are stored for later use in the computer.

OBJECT OR OBJECTS

It is one object of at least one embodiment to provide a method for determining vision defects and for collecting data for correcting vision defects of the eye by interaction of a patient with an examiner and apparatus therefor.

It is also an object of at least one embodiment in one aspect to make available a method, and apparatus, which serve in the acquisition of correction data for the correction of eye aberrations, with the translation of such data leading to an improved faculty of vision of the patient.

SUMMARY OF THE INVENTION

One feature of at least one embodiment to accomplish the foregoing objects resides in a method for determining vision defects and for collecting data for correcting vision defects of the eye by interaction of a patient with an examiner, said method comprising: projecting an image into the eye of the patient with an adaptive optical system; said adaptive optical system comprising at least one adaptive optical element; said at least one adaptive optical element being configured to have its optical characteristics changed by an electrical signal, in an attempt to minimize distortions of the image as perceived in the eye and the brain of the patient; determining the presence of distortions of the image as perceived in the eye and the brain of the patient by interaction of the patient with the examiner; providing an electronic control system; said electronic control system being configured to control the optical characteristics of said at least one adaptive optical element through outputting of an electrical signal; modifying the optical characteristics of said at least one adaptive optical element through outputting of an electrical signal of said electronic control system and obtaining a modified image of the image in the eye of the patient, in an attempt to correct for the distortions of the image as perceived in the eye and the brain of the patient; evaluating said modified image by interaction of the patient with the examiner; repeating said modifying step and said evaluating step and obtaining a modified image having minimized distortions as perceived in the eye and the brain of the patient; determining the optical characteristics of said at least one adaptive optical element, as modified, resulting from said modified image having minimized distortions as perceived in the eye and the brain of the patient; and computing vision correcting data for the eye being examined, from said optical characteristics of said at least one adaptive optical element, as modified, resulting from said modified image having minimized distortions as perceived in the eye and the brain of the patient.

Another feature of at least one embodiment to accomplish the foregoing objects resides in a method for determining vision defects and for collecting data for correcting vision defects of the eye by interaction with a patient, said method comprising: forming an image in the eye of the patient with an optical system; said optical system being configured to have its optical characteristics changed by at least one signal, in an attempt to minimize distortions of the image as perceived in the eye and the brain of the patient; determining the presence of distortions of the image as perceived in the eye and the brain of the patient by interaction with the patient; providing an electronic control system being configured to control the optical characteristics of said optical system through outputting of at least one signal; modifying, at least once, the optical characteristics of said optical system through outputting of at least one signal of said electronic control system and obtaining a modified image of the image in the eye of the patient, in an attempt to correct for the distortions of the image as perceived in the eye and the brain of the patient by interaction with the patient; determining the optical characteristics of said optical system, as modified, resulting from said modified image of the image in the eye of the patient having minimized distortions as perceived in the eye and the brain of the patient; and computing vision correcting data for the eye being examined, from at least one signal indicating said modified optical characteristics of said optical system.

A further feature of at least one embodiment resides in an apparatus for determining defects of the retina of the eye by interaction between a patient and an examiner, said apparatus comprising: an adaptive optical system configured to form an image in the eye of the patient; said adaptive optical system being configured to have its optical characteristics changed by at least one signal, in an attempt to compensate distortions of the image due to aberrations of the eye and thus defining a first set of aberration data which correspond to the objective aberrations of the eye; an electronic control system operatively connected to said adaptive optical system; said electronic control system comprising an arrangement configured to modify, at least once, the optical characteristics of said adaptive optical system, and being configured to output at least one signal to obtain a modified image, in an attempt to correct for the distortions of the image as perceived by the patient through interaction with the patient in a subjective assessment thus defining a second set of adaptive data; and an apparatus configured to compare the first set of aberration data and the second set of adaptive data and to determine the regions of the retina related to these sets of data in which these sets of data are different.

A further feature of at least one embodiment resides in an apparatus for determining vision defects and for collecting data for correcting vision defects of the eye by interaction between a patient and an examiner, said apparatus comprising: an adaptive optical system configured to form an image in the eye of the patient; said adaptive optical system being configured to have its optical characteristics changed by at least one signal, in an attempt to minimize distortions of the image as perceived in the eye and the brain of the patient; an electronic control system operatively connected to said adaptive optical system; said electronic control system comprising an arrangement configured to modify, at least once, the optical characteristics of said adaptive optical system, and being configured to output at least one signal to obtain a modified image, in an attempt to correct for the distortions of the image as perceived in the eye and the brain of the patient through interaction with the patient; an arrangement configured to determine the optical characteristics of said adaptive optical system, as modified, resulting from said modified image formed in the eye of the patient having minimized distortions as perceived in the eye and the brain of the patient; and an apparatus configured to compute vision correcting data for the eye being examined, from at least one signal indicating said modified optical characteristics of said adaptive optical system.

More particularly, the object in accordance with at least one embodiment is accomplished by an apparatus for determining defects of the retina of the eye by interaction between a patient and an examiner, said apparatus comprising: an adaptive optical system configured to form an image in the eye of the patient; said adaptive optical system being configured to have its optical characteristics changed by at least one signal, in an attempt to compensate distortions of the image due to aberrations of the eye and thus defining a first set of aberration data which correspond to the objective aberrations of the eye. With this set of data, the objectively corrected eye is described. The objective compensation of the eye can be accomplished by objective metrological methods as described. This data can be defined by the characteristics of the adaptive optical system, i.e. the positions of the mirrors of the adaptive optical system compensating for the objective aberrations. It is possible to define this data by an image of the retina at this stage, in which the objective defects of the eye are compensated by the adaptive optical system. In general, this image is a well focused image of the retina since all optical defects of the eye are perfectly or almost perfectly compensated. Further, it is provided for an electronic control system operatively connected to said adaptive optical system; said electronic control system comprising an arrangement configured to modify, at least once, the optical characteristics of said adaptive optical system, and being configured to output at least one signal to obtain a modified image, in an attempt to correct for the distortions of the image as perceived by the patient through interaction with the patient in a subjective assessment thus defining a second set of adaptive data. This second set of data now describes the compensation as it seems best for the patient. This set of adaptive data might differ from the set of aberration data or it might be identical. In case the set of data differ from each other, this might be an indication that the patient feels that a different compensation might be better than the objectively best compensation for the eye as an optical system. Thus, this difference indicates that the patient compensates in the defined amount with the brain. This might be caused by a defect of the retina in special regions or areas for which the brain already compensates the signal and information that is delivered from the retinal receptors, the cones and/or rods. Thus, this difference indicates that the cones and rods in these areas are affected. Further, it is provided for an apparatus configured to compare the first set of aberration data and the second set of adaptive data and to determine the regions of the retina related to these sets of data in which these sets of data are different. Thus, it is now possible to compare these two sets of data and the differences of these two sets indicate the regions of the retina that might be negatively affected. In case that an image of the retina is taken as the data, it is possible to see from the second image, i.e. the image after subjective compensation, areas which are not well focused but blurred. These areas correspond to the regions of the retina that are negatively affected. The areas that are well focused on the image after subjective compensation work normally. In this case, the subjective impression and the objective compensation is identical or substantially identical. In case that the data set is defined by the characteristics of the adaptive optical system, the difference can be found in for instance the different positions of the micromirrors or the optical elements of the adaptive optical system. With these differences it is possible to calculate the areas or regions on the retina that are affected. Especially, from this difference the amount of visual neuronal function and behavior can be shown in comparison to the optical quality of the examined eye. Thus, this apparatus is essentially ideal to find already defect sensors in the eye, especially in the macula, without the patient realizing this defect at the moment—since the patient compensates with the brain for these defects, which can be of use with the early diagnosis of glaucoma. In at least one possible embodiment, these tests are carried out for different colors or color channels. Thus, the function of the sensors of the macula can be examined.

A further arrangement is provided that is configured to determine the optical characteristics of said adaptive optical system, as modified, resulting from said modified image formed in the eye of the patient having minimized distortions as perceived by the patient defined by the second set of adaptive data; and/or an image sensor configured to register an image of the retina of the eye, especially a fundus camera, a confocal laser scanner or an optical coherence tomograph. With this arrangement it is possible to collect the data sets either as the characteristics of the adaptive optical system or as an image of the retina. With a fundus camera, especially a fundus camera with an adaptive optic (AO), a high-resolution image can be taken. High-resolution images can also be achieved with the help of a confocal laser scanner or an optical coherence tomography apparatus. With these high-resolution images it is possible to detect the smallest or very small differences between the image of the objectively compensated image or picture and the image according to the subjectively optimized set up.

In at least one possible embodiment, the adaptive optical system further comprises a monitor to visualize the regions of the retina of the eye related to these sets of data in which these sets of data are different, especially by color coding these regions. Thus, it is possible to connect a monitor and to show a picture of the retina. Within this picture, the areas in which differences between the objective compensation and the subjective impression are found, can be shown in color. In at least one possible embodiment, the color indicates the degree of difference between the two data sets at this point. Thus, the spectator can visualize easily the areas in which the sensors of the retina are affected and the color indicates to which amount the areas are affected. These tests can be carried out for different colors (blue, red, green) to test the different cones of the macula on the retina. Thus, the objective monochromatic aberrations are measured in the center of the respective spectral sensitivity or responsiveness, i.e. the macula.

More particularly, the object in accordance with at least one embodiment is accomplished by an apparatus for the determination of correction data for the correction of eye aberrations of a patient, said apparatus comprising an optics system, and the apparatus further comprising an adaptive optics, and/or a wavefront modulator, as well as an arrangement for the display of test images, to be displayed by way of the adaptive optics, and a control system. This apparatus makes it possible for test images to be shown to the patients, by means of the adaptive optics, which test images can be evaluated in subjective manner by a patient. By way of the subjective assessment of the test images that are displayed on the adaptive optics, minute aberrations of the eye can be recognized and the correction that has been determined by the patient as subjectively most suitable compensation of eye aberrations can be determined. The alignment or position of the adaptive optics at the moment in which the corrections are perceived as subjectively optimum conditions, accordingly, corresponds to the correction data for the correction of eye aberrations.

The optical system serves to align and/or focus the direction of rays from the eye to the adaptive optics. Such an optical system may be provided, for example, by an arrangement of lenses.

In at least one possible embodiment, the adaptive optics is a modulator, particularly, a wavefront modulator. Such adaptive optics can be realized in various embodiments. Thus, there are available transmitting modulators based on LCD-basis, or reflecting modulators having moveable membranes. These modulators with moveable membranes can be classified on the basis of their control, for example, piezoelectric, electrostatic, and bimorph membranes. Electrostatic membrane mirrors may be used to configure the adaptive optics, or electrically controlled micro-mirror arrays. Reflecting and also transmitting media may be employed to configure the adaptive optics.

The arrangement for the display of test images by means of the adaptive optics may comprise, in the case of reflecting elements of the adaptive optics, a projector, which projects the test images onto the reflecting elements of the adaptive optics, which test images then reach the eye by way of the optical system. In the case of an adaptive optics with transmitting media, a projector is contemplated which projects through the adaptive optics onto the eye. It is furthermore possible, in the case of an adaptive optics with LED-display, for the arrangement for the display of test images to utilize electrical signals which generate corresponding test images and/or portions of such test images on the individual LED-surfaces.

In at least one possible embodiment, the test images are configured in such a way that they react, in reference to the aberrations that are to be investigated, particularly pronounced to the modulated wavefront through the adaptive optics. Thus, in the test image a portion of an image error can be traversed in scanning mode and the wavefront can be deformed in such a way that only one individual image error is changed or compensated. By way of the test image that has been determined by the patient, by way of iterative analysis, to be subjectively the most distortion-free test image, a subjectively aberrations-free image is produced on the eye.

The control system, in at least one possible embodiment, is a computer. The adaptive optics can be controlled by way of the control system, and with it one can determine the correction data for the correction of eye aberrations. This control system may comprise a computer which controls n×m micro-optics elements, whereby each element can be individually controlled in terms of angle of inclination and in terms of adjustment of height. This means that the wavefront can be changed in a localized defined manner.

The correction data may be utilized to determine an optimal, patient-specific, refractive element. Refractive elements may comprise IOLs (intra ocular inserts), ICLs (implantable contact lenses), contact lenses, and spectacle glasses. In one possible embodiment, the correction data are utilized to determine the beam alignment for a contemplated laser treatment of the eye, particularly of the cornea.

In one possible embodiment, the adaptive optics is comprised of a plurality of mirrors that can be individually adjusted. These individual mirrors can be positioned in conformity with the subjective judgement of the patient in such a way that the mapped test image is subjectively and optimally viewed by the patient. Thus, by means of the adaptive optics, the selected test images, and the corresponding evaluation algorithms, the actively physiologically evaluated mirror positions can be converted into correction data for a correction of eye aberrations, so as to provide an optimal faculty of vision for a patient. The mirror positions in their entirety define a data set which describes that correction that has been sensed to be the optimal correction, based on the adaptive optics: the adaptive data.

In one possible embodiment, the adaptive optics is configured substantially as a segment of a sphere. This makes it possible to determine the correction data from the normals of the positioned mirrors, because the adaptive optics in the configuration of a segment of a sphere corresponds directly to the outer shape of the eye. This obviates otherwise required conversion of the sensed parameters into the correction data.

In at least one possible embodiment, a control system is contemplated, which serves to align or adjust the position or attitude of the adaptive optics. In this manner, through changes of the individual mirrors any aberration behavior or condition of an eye can be compensated and the test images for specially preselected aberrations in the human eye thus displayed can be processed. By means of this control system it is also possible to display predetermined sets of aberrations of higher-orders and these can be evaluated in a dialogue with the patient. In at least one possible embodiment, by means of the control system, the adaptive optics, in the scanning mode, tests a series of eye aberrations, to thereby determine the optimal setting of the adaptive optics for an optimal faculty of vision of the patient.

In at least one possible embodiment, the embodiment comprises an aberrations measuring arrangement, particularly an aberrations measuring device, such as, an aberroscope or aberrometer, for the determination of aberration data which correspond to the objective aberrations of the eye. Such aberrations measuring arrangements, for example, refractometers, or aberroscopes, and/or wavefront analyzing or measuring apparatus, can determine the objective eye aberrations and, for verification of the computed correction values of the patient, they can be confirmed or corrected by the patient by way of an adaptive optics.

Thus, in accordance with one aspect of the invention, subjective correction values, obtained by means of an adaptive optics, and objective correction values, obtained by means of an aberroscope, can be advantageously combined.

In at least one possible embodiment, the correction data for the correction of eye aberrations are determined by means of a second control system. In at least one possible embodiment, this second control system comprises a computer. By means of applicable software, the set of correction data can be established, on the basis of adaptive data or, respectively, aberration data. In at least one possible embodiment, the aberration data are determined as rough or approximate values, so at to determine the adaptive data, by way of a subjective assessment of the test images, by means of the adaptive optics, and to utilize such adaptive data as basis for the correction data. It is also within the scope of the invention that use is made of the average or mean value of the adaptive data and of the average or mean value of the aberration data as the basis for the correction data.

The object of one aspect of the present invention is also particularly accomplished by a method for the determination of correction data for the correction of eye aberrations, in which method in a first step are determined, by means of an adaptive optics, adaptive data relating to a subjectively optimal correction adjustment of the eye, and in a further step are determined the correction data for the eye corrections which correction data are based on the adaptive data. It is an advantage of this method that the correction data are obtained in an a priori active, physiologically assessed metrological method, such correction data serving to correct vision defects of the eye, such vision defects negatively impacting the faculty of vision. This means that no longer does use need to be made of an error-prone determination of objective display errors in a dynamic-organic display apparatus in which determination no use is made of the characteristics, or features, of the signal processing by the human nervous system, respectively the brain. In a dialogue with the patient, in accordance with one aspect of the invention, by means of the adaptive optics, those values are determined which correspond to the optimal correction condition; this may be different from the condition which was found to be the optimal condition in an objective assessment.

In at least one possible embodiment, additional aberration data are gathered which correspond to the objective aberrations of the eye and the correction data are determined on the basis of the adaptive data and the aberration data. By way of a comparison of the subjectively determined data and the objectively determined data, it is possible to point to the importance of the physiological influences of the image processing.

In at least one possible embodiment, with the aid of objective metrological methods, using the aberrations measuring arrangements or, respectively, the mentioned measuring devices, the coarse or significant correction values are determined and they are utilized as a starting point for the further determination of the final correction data by way of the subjective method, that is, a method comprising an active physiological assessment.

In at least one possible embodiment, the adaptive data for a subjectively optimal correction condition of the eye are obtained by a subjective assessment of modified test images by the patient, modified by the change of mirror positions of mirrors of the adaptive optics. The change of the mirror position of the individual small mirrors allows one to compensate for any aberration condition of the eye. The position of the individual small mirrors, or micromirrors, is then establishing that condition which affords the maximum of compensation for the eye aberrations of the patient. The position parameters of the individual small mirrors, accordingly, correspond to the subjectively optimal correction of the eye aberrations. These position parameters of the mirrors can easily be captured and provide a good utilization basis for the determination of the adaptive data and/or the correction data.

The above-discussed embodiments of the present invention will be described further hereinbelow. When the word "invention" is used in this specification, the word "invention" includes "inventions", that is the plural of "invention". By stating "invention", the Applicants do not in any way admit that the present application does not include more than one patentably and non-obviously distinct invention, and maintains that this application may include more than one patentably and non-obviously distinct invention. The Applicants hereby assert that the disclosure of this application may include more than one invention, and, in the event that there is more than one invention, that these inventions may be patentable and non-obvious one with respect to the other.

BRIEF DESCRIPTION OF THE DRAWINGS

The invention is explained in greater detail below with reference to the embodiments which are illustrated in the accompanying drawings.

FIG. 11 is a view similar to FIG. 2a and illustrating a portion of a micromirror device;

FIG. 12 is a view similar to FIG. 2b and illustrating details of the micromirror interface actuation.

DESCRIPTION OF THE EMBODIMENT OR EMBODIMENTS

Figure 1A:
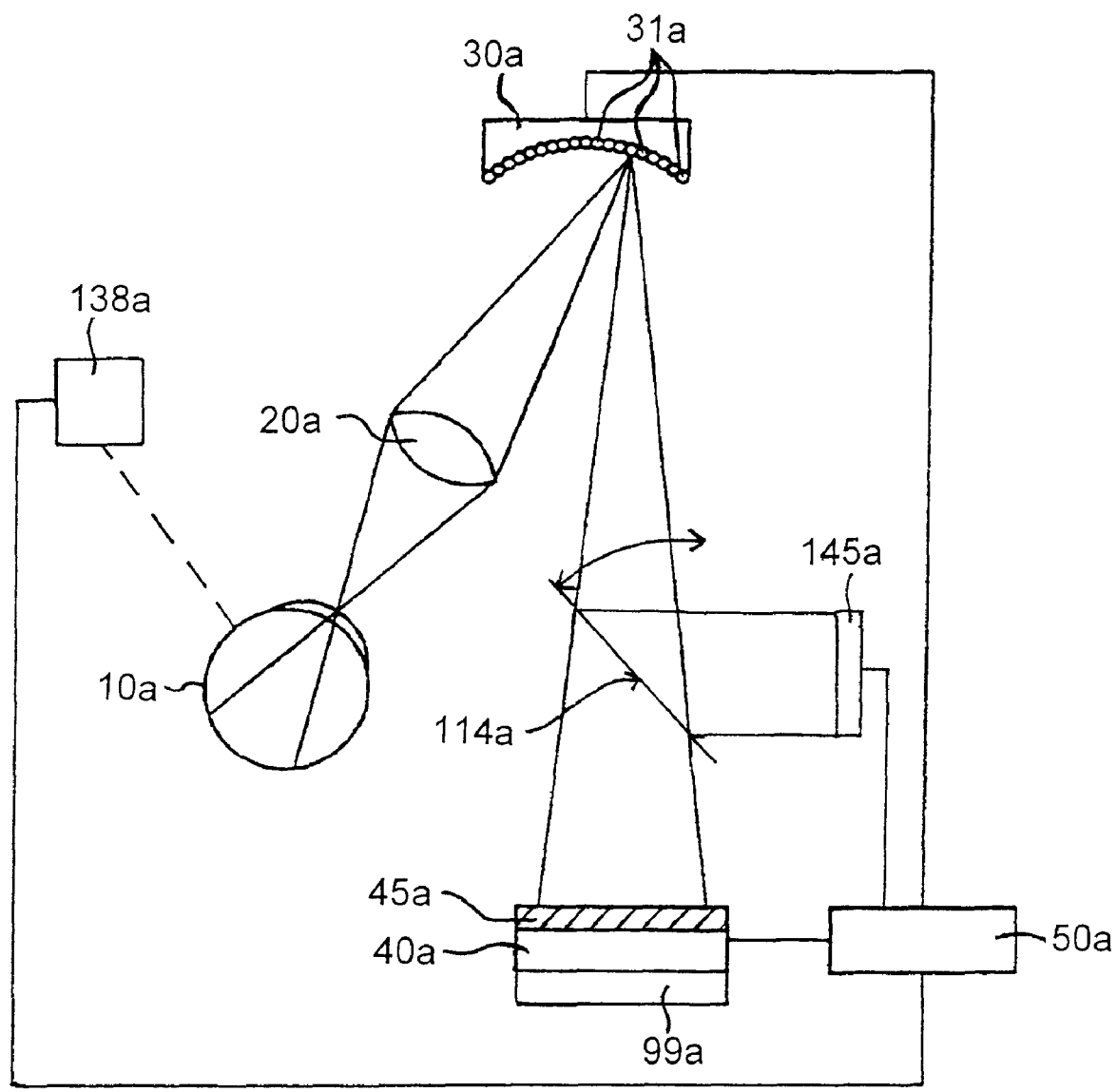
FIG. 1A is a block circuit diagram of an apparatus in accordance with at least one possible embodiment.
Figure 1:
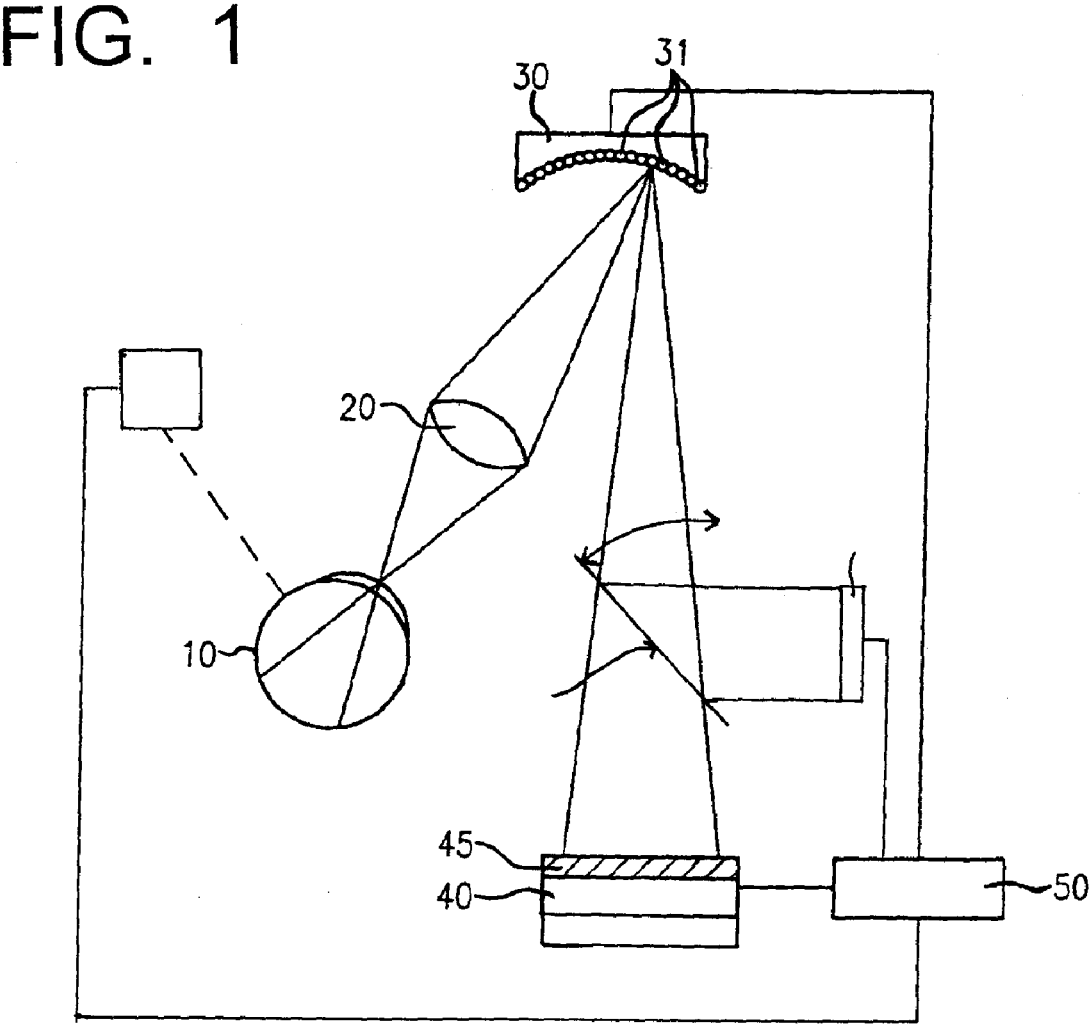
FIG. 1 is a block circuit diagram of an apparatus in accordance with at least one possible embodiment.

FIG. 1 is a block circuit diagram of an apparatus embodiment in accordance with at least one possible embodiment. The eye 10 considers, via a lense 20, a mirror-field, or an array of mirrors, of an adaptive optics 30 comprised of individual mirrors 31. An arrangement 40 for the projection of test images selectively produces test images 45. A control system 50 is connected to the arrangement 40 for the projection of test images and to the adaptive optics 30.

The test image 45 is produced by way of the arrangement 40 for the projection of test images and is projected onto the adaptive optics 30. The individual mirrors 31 project the test image, via lens 20, onto the retina of the eye 10. The control system 50 captures the attitude of the individual mirrors 31 and the selection of the test image 45.

The patient now judges the subjective or actual quality of the image of the test image 45 on the retina of the eye 10, in at least one possible embodiment, by responding with "good" or "bad" in response to the projected test image. If he guesses a requirement for correction, by way of the control system 50, the position of individual mirrors 31 is modified until the image of the test image on the retina of the eye 10 is shown in optimal manner. The position of the individual mirrors 31 is then is utilized as value-tuple for the adaptive data of this test image 45 and corresponds to the correction of the aberrations for the test image 45 being viewed, this correction being considered to be the optimally sensed correction.

By comparing the two data sets at the beginning (objective compensation) and the end (adaptive data), an early diagnosis can be made with respect to the retina and a possible glaucoma.

In at least one possible embodiment, the positioning of the individual mirrors into the position which corresponds to the optimal position is done by way of a scanning mode. In this, the patient is shown, in the scanning mode, with the aid of evaluation algorithms, tolerance fields of image-errors, and the optimal positioning of the adaptive optics is determined. The evaluation algorithms are separated in conformity with individual image errors.

FIG. 1A is a block circuit diagram of an embodiment of an apparatus in accordance with another aspect of the invention. The set up is similar to the one in FIG. 1—all elements of FIG. 1 are also present in the set up of FIG. 1A.

Additionally, an image sensor 145a is provided in a conjugated plane to the plane of the test image 45a. In at least one possible embodiment, the image sensor 145a comprises a CCD or CMOS element. The image sensor 145a is connected to the control system 50a. The control system 50a is also connected to the adaptive optical system 30a with mirrors 31a. A mirror 114a is provided that can be pivotally moved between two positions. In the first position (shown in FIG. 1A) the image of the retina of the eye 10a is captured on the image sensor 145a. In the second position (indicated by the arrow), the optical path is directed to the test image 45a as in the set up of FIG. 1. Further, a correction element 138a is provided that, in at least one possible embodiment, comprises input elements for the patient to input feedback according to the subjective assessment of the test image 45a by the patient. This correction element 138a is also connected to the control system 50a.

In a first step, the objective correction or compensation of the aberration of the eye 10a is preset by adjusting the mirrors 31a of the adaptive optical system 30a via the control system 50a. For this situation, a first set of data is collected by the fundus camera as image sensor 145a, i.e. a picture of the retina of the eye 10a is taken by the image sensor 145a with the mirror 114a being in the first position as shown in FIG. 1A.

In a second step, mirror 114a is moved to the second position. A test image 45a is projected by the arrangement 40a via the adaptive optical system into the eye 10a of the patient. This test image 45a is now objectively fully compensated or corrected or substantially fully compensated or corrected by the adaptive system 30a.

In a third step, the patient is asked to assess the quality of the test image 45a. The patient corrects the felt visual defects by inputting amendment data into the correction element 138a. This data is transferred to the control system 50a and causes changes in the characteristic of the adaptive optical system 30a by changing the position of at least on of the mirrors 31a when such compensation is required. At the end, the patient confirms via the correction element 138a that the test image 45a is now fully focused or substantially fully focused and that with this configuration of the adaptive optical system the best compensation is achieved.

For this configuration, a second set of data (adaptive data) is recorded, i.e. a second image of the retina of the eye 10a is taken by the image sensor 145a. Therefore, the mirror 114a is brought into the first position (as shown in FIG. 1A) and a picture is taken via the adaptive optical system in the second configuration.

Now, the first data set and the second data set are compared, i.e. the first picture of the retina with the correction data set and the second picture of the retina with the adapted data set are compared to each other. The differences in these pictures are ascertained.

These differences are now visualized, in at least one possible embodiment, on a monitor (not shown) showing the picture of the retina with marks which refer to the areas or regions of the retina where these differences appear. These areas are then taken as the areas in which the retina shows defects that are compensated for by the brain of the patient and not the optical system of the eye 10a. Thus, these areas indicate in an early diagnosis where there might be first signs for glaucoma.

Figure 2A:
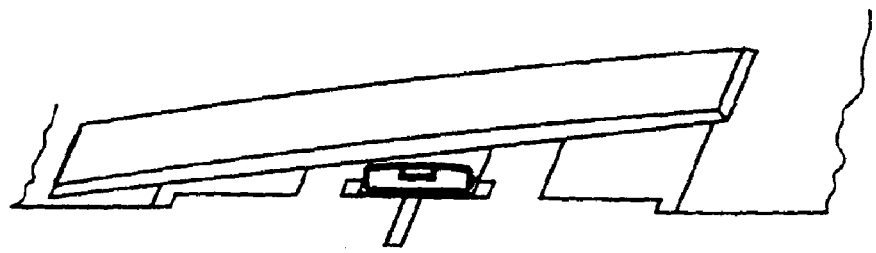
FIG. 2a illustrates a mirror of an adaptive optics.

FIG. 2a shows a single mirror 31 of an adaptive optics 30. This mirror has an approximately square base surface. The length of the sides of the mirror 31 is approximately 100 micrometers. In at least one possible embodiment, this mirror 31 is produced monolithically atop a circuit comprising customary CMOS SRAM cells, (complementary metal oxide semiconductor, static random access memory). The mirror 31 is actuated by electrostatic forces which are produced by application of a voltage difference, or potential difference, between the mirror plate and the electrode. In at least one possible embodiment, piezo-electric effects are utilized to fix the position of a single mirror. These mirrors 31 of the adaptive optics 30 are suited to balance tilt errors.

Figure 2B:
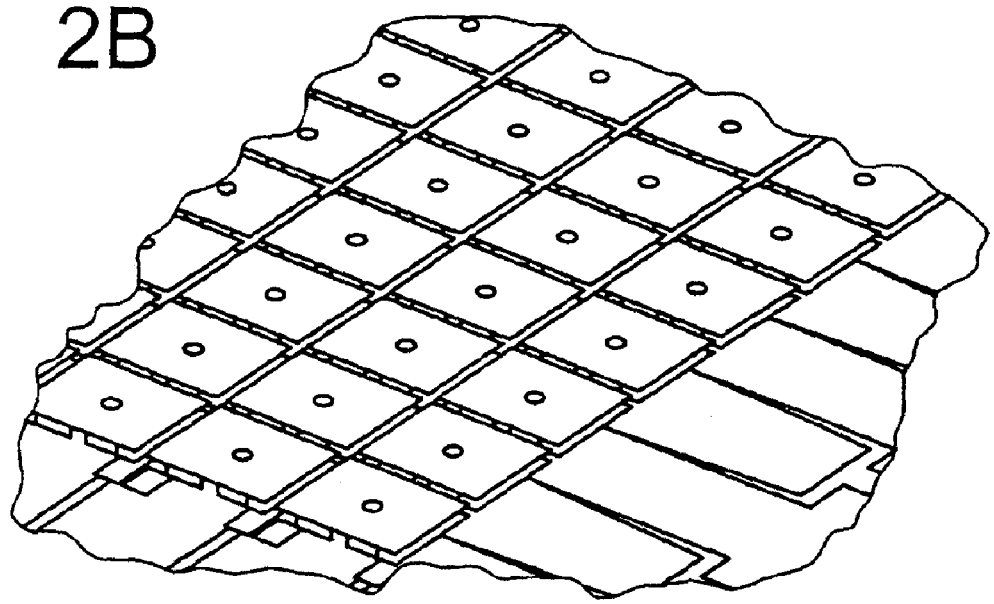
FIG. 2b shows a portion of an array of mirrors of the type illustrated in FIG. 2a, together forming an adaptive optics.

FIG. 2b shows a portion of an array of mirrors 31 of the type illustrated in FIG. 2a which together configure an adaptive optics 30. The mirrors 31 are arranged edge-to-edge in a mirror field and thus provide a coherent or continuous mirror field or surface, but with each micromirror or small mirror 31 being configured to be individually adjustable. This allows compensation of higher-order aberrations of the eye 10. The positions of the individual mirrors 31 in the situation that the patient considers to be the best condition of the test image correspond as value-tuples to the adaptive data. This constellation of the adaptive optics, that is, the position of all mirrors 31 of the full array of mirrors, is transferred to the control system 50 and converted into correction data.

In at least one possible embodiment, the adaptive optics, that is, the array of mirrors, has a contour which corresponds to the top surface of the cornea of the eye 10. For example, this contour may be that of a segment of a sphere. This means that the normals of the individual mirrors 31 can be used to provide the adaptive data, this simplifying a conversion of the individual data of the mirror positions.

Figure 3:
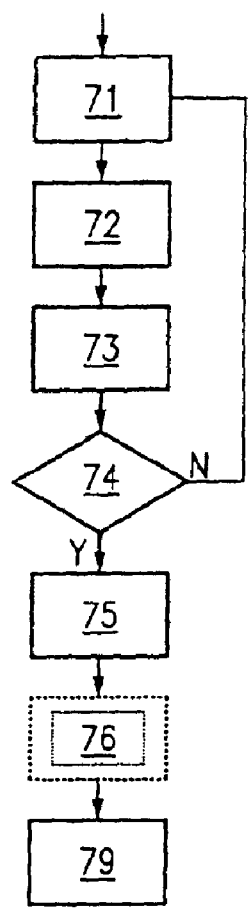
FIG. 3 is a flow diagram of a method according to at least one possible embodiment.

FIG. 3 is a flow diagram for the illustration of an embodiment of the method in accordance with at least one possible embodiment. With this embodiment 70, in step 71 a test image is loaded which test image is mapped on the eye 10 via the adaptive optics 30, by way of the arrangement 40 for the display of test images. In step 72 the adaptive optics 30 for this test image 45 is varied until the subjectively optimal adjustment has been found. This adjustment which has been found to be the subjectively optimally sensed adjustment is thus ascertained, or determined, and this adjustment is correspondingly stored in step 73. An inquiry is made in step 74 whether the optimal wavefront correction has already been attained or whether further aberrations need to be corrected. This can be done on the basis of an estimation by the patient, or this can be decided on the basis of processing of a series of predetermined test images, which test images are suited to reveal special mapping errors. Once no further test images need to be processed, there are computed, in step 75, the adaptive data 35 that are obtained from the various mirror positions of the adaptive optics 30. This is accomplished, in at least one possible embodiment, by a method in accordance with the Zernike polynomial or the Taylor polynomial.

In at least one possible embodiment, in step 79, the correction data 55 is determined from the adaptive data 35. In at least one possible embodiment, the correction data for the determination of beam direction coordinates of a laser system 60 is utilized for the correction of the eye 10.

In at least one possible embodiment, in a step 76 there are determined aberration data 85, by way of an objective measuring method, and/or also via an aberrations measuring arrangement or an aberroscope or aberrometer 80 to determine aberrations, and these data 85 are also considered, in step 79, in the determination of the correction data 55.

Figure 4A:
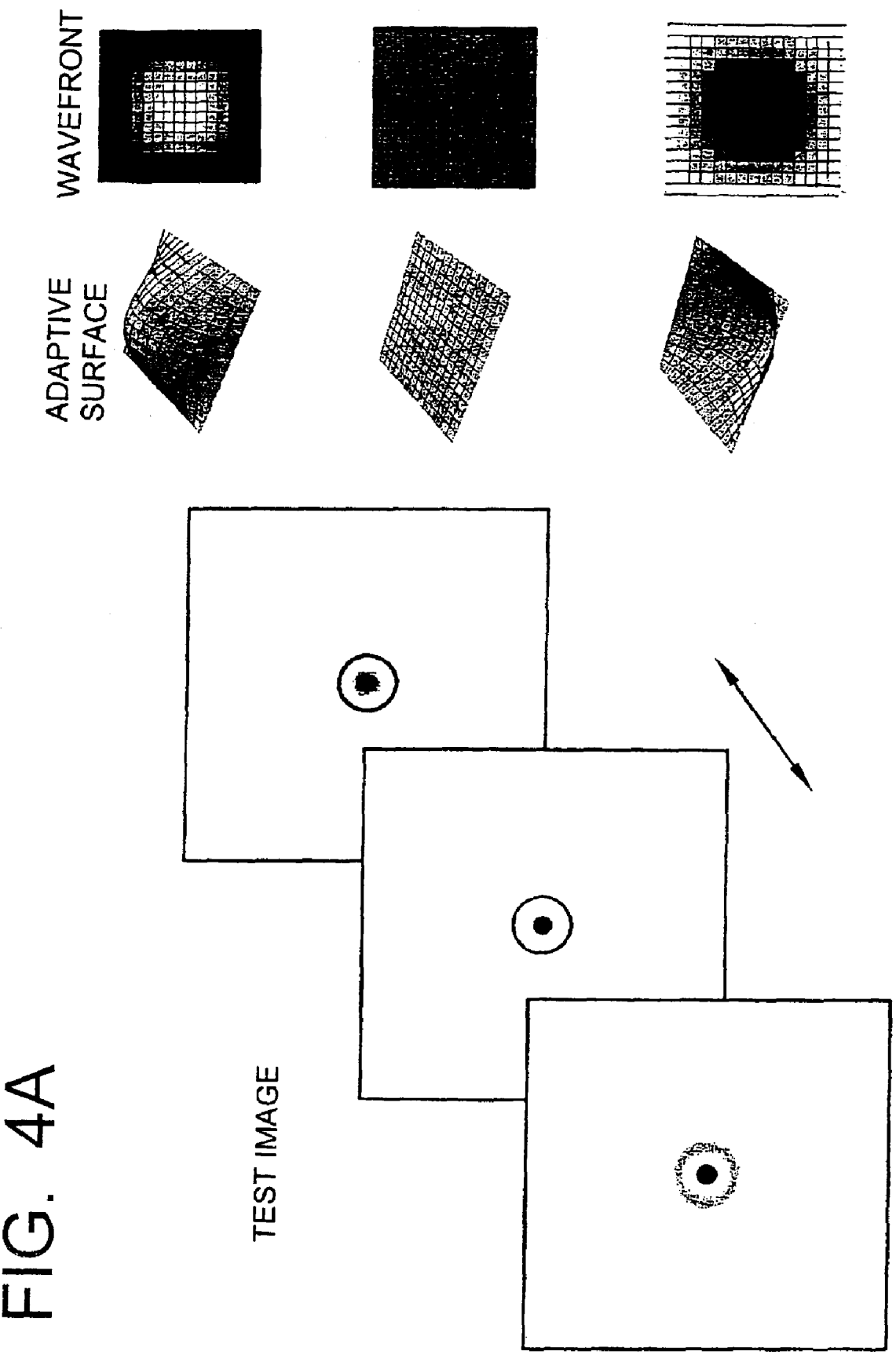
FIG. 4a is an illustration of a first test image with associated adaptive surface and wavefront in three conditions.

In FIGS. 4a, b, and c are illustrated examples of three different test images together with the corresponding adaptive surface and the corresponding wavefront, the illustration respectively depicting three conditions. Test images in various states of deformation are shown in the three rows of the individual figures. A test image as would be seen with an eye free of aberrations is shown in the left column. The geometry of the adaptive surface which would give rise to a distortion of the test image for the eye free of aberrations is illustrated in the central column; the corresponding wavefront is illustrated in a matrix in the right column using a gradation of gray values.

A central point and a ring centered about the point are shown in the case of the test image of FIG. 4a. In the illustration in the central row, the adaptive optics is aligned in a planar manner, as can be seen in the central column of the central row, and does not modulate the wavefront. This can readily be seen in the representation of the wavefront in the right column. The test image in the left column, accordingly, is not distorted, and it is clear. In the top row the adaptive surface comprises a localized maximum at the center. Accordingly, the wavefront is shifted to the center and the test image is seen in distorted manner in the center. In the case of a viewer whose eye has a correspondingly differently oriented, or configured, aberration, this test image would be seen to be without distortion, which leads to the recognition of his particular aberration. In the lowermost row, the adaptive surface contains a localized minimum in the center, such that a correspondingly different aberration is being compensated.

By means of the control of the adaptive optics in such a way that a test image error portion is traversed in a scanning mode, that is, for example, from the adaptive surface in the first line over the second line to the third line and back, the wavefront is deformed in such a way that only one image error is changed. The patient now searches in an iterative manner that test image that is subjectively free of distortions. An image which is subjectively free of distortions is thus created by way of an overlay of the wavefront aberrations. In this manner, conclusions can be drawn, based on the shape of the adaptive surface and/or the wavefront corresponding thereto, with respect to the eye aberrations of the patient. In at least one possible embodiment, the spherical lens correction is performed first by a pattern generated by modifications of the image by the signal converter 46 in response to signals from the control system 50. Second, astigmatism is corrected in an analogous manner by the signal converter 46 and the control system 50. Subsequently, the higher-order distortions or aberrations can be corrected one after another by modifying the signals from the signal converter 46 by the control system 50.

Figure 4B:
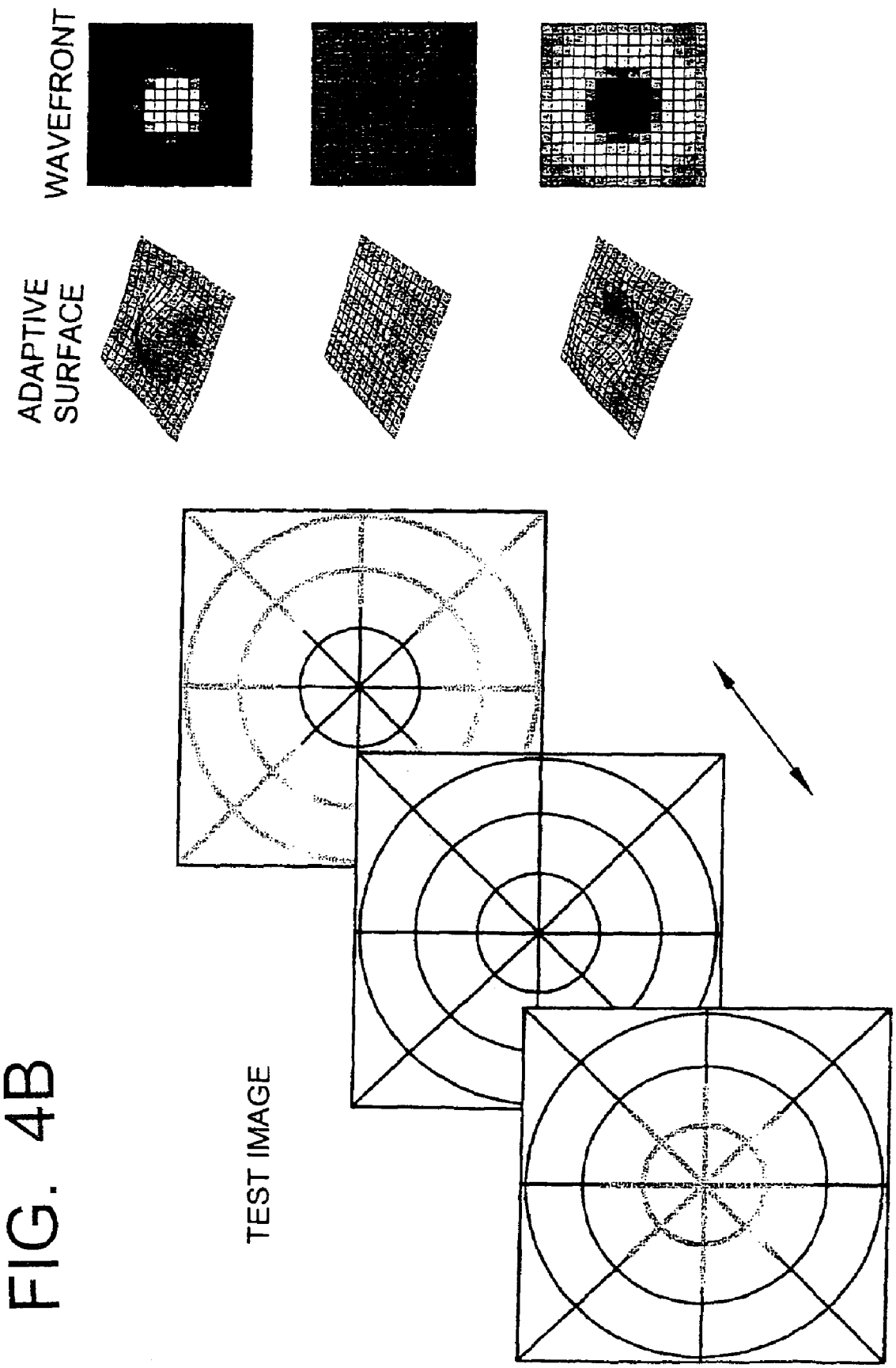
FIG. 4b is an illustration of a second test image with associated adaptive surface and wavefront in three conditions.
Figure 4C:
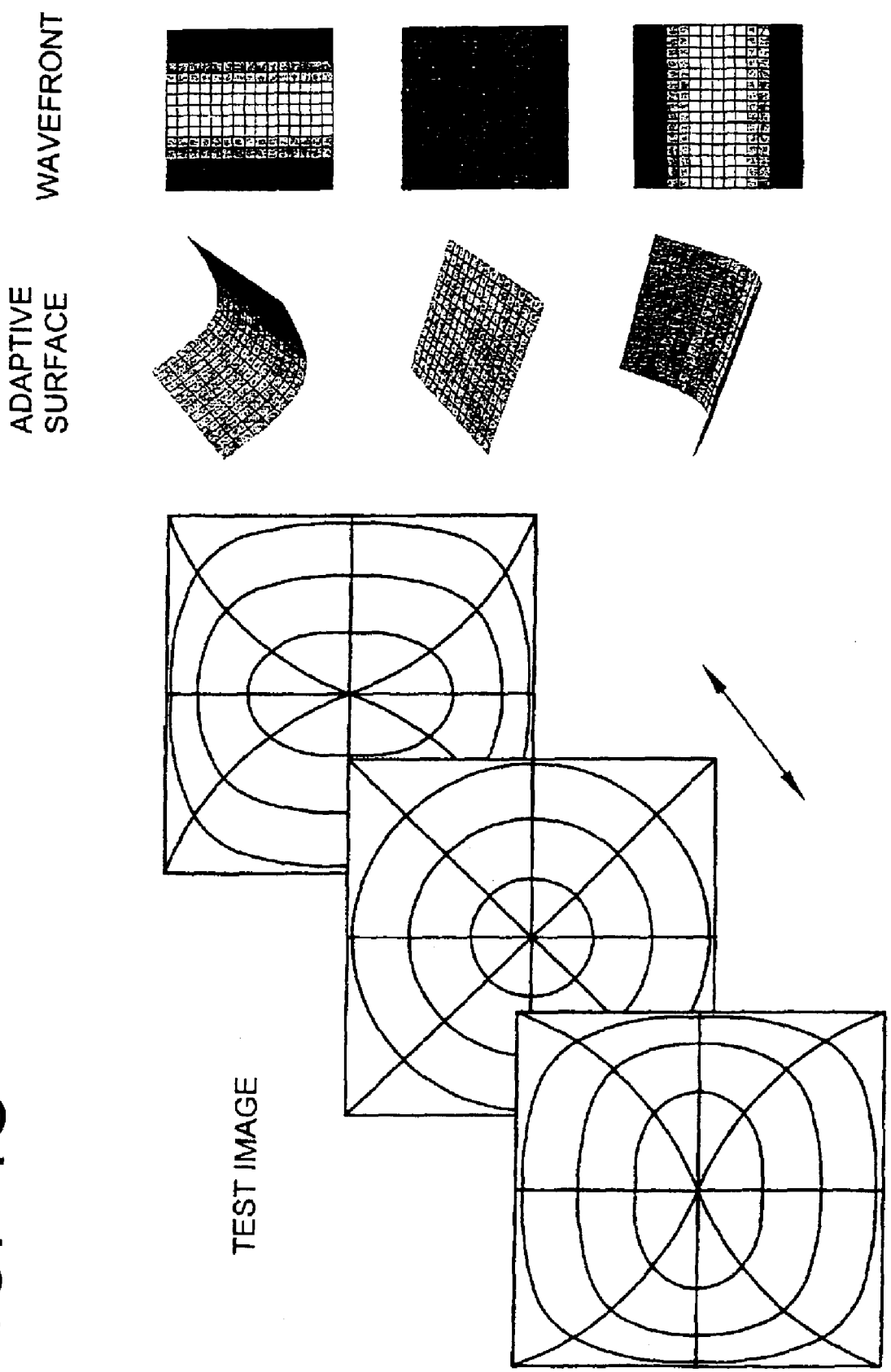
FIG. 4c is an illustration of a third test image with associated adaptive surface and wavefront in three conditions.

Further test images for other image errors are shown in FIGS. 4b and c. For these are then given the correspondingly modified adaptive surfaces and the corresponding wavefronts. The considerations applicable to the test image according to FIG. 4a apply in analogous manner.

Figure 5:
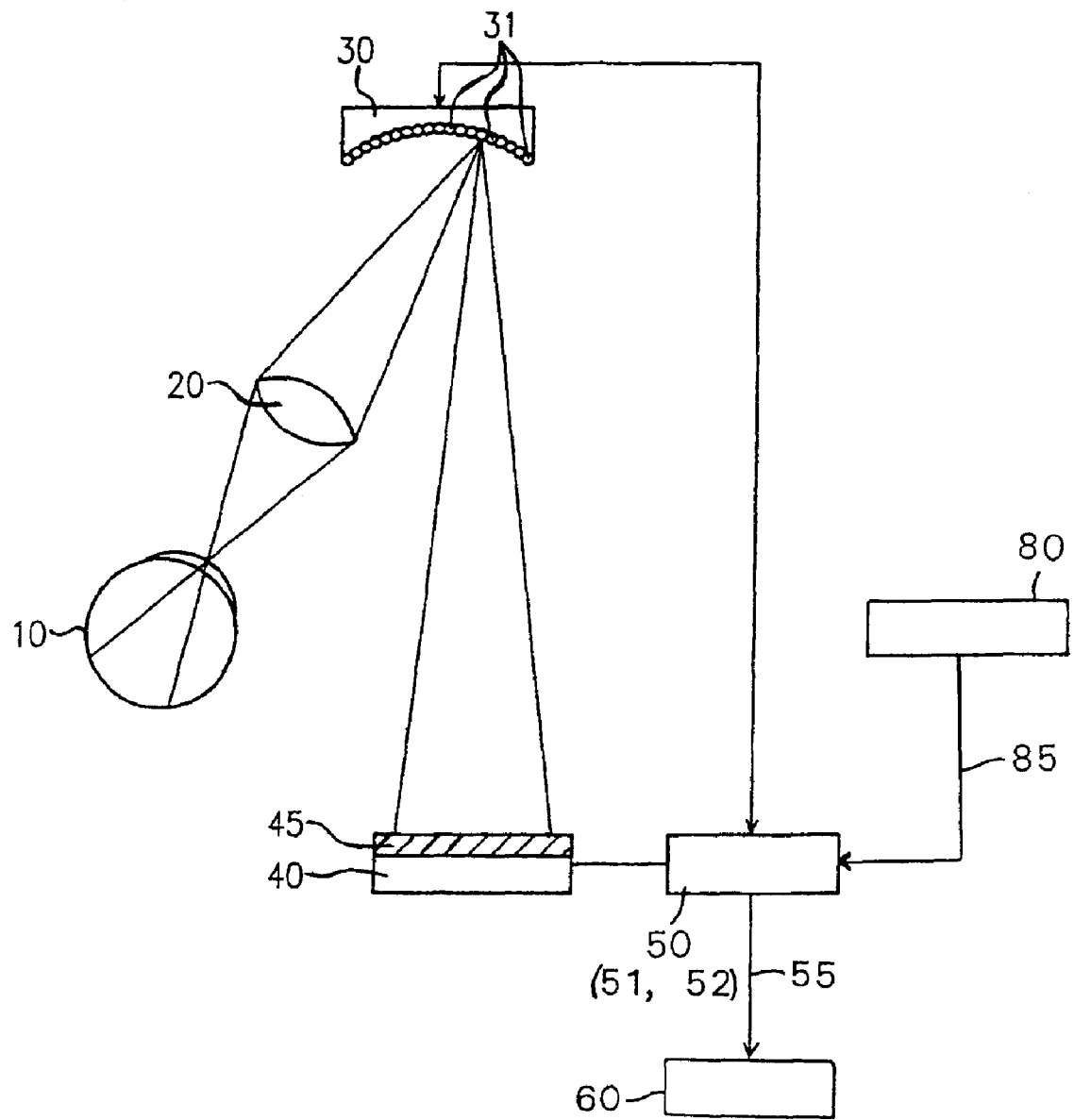
FIG. 5 is a diagram illustrating the adaptive optical system in conjunction with an aberrometer.

FIG. 5 illustrates a further embodiment of the apparatus according to at least one possible embodiment. The eye 10 considers, via lens system 20, an image 45 projected by projector 40 onto an array of mirrors 31 of the adaptive optics 30. Signals are passed from adaptive optics 30 to a control system 50 indicative of the position of the individual mirrors 31. Signals can be passed from the control system 50 to the mirrors 31 to change the optical characteristics of the mirrors 31 in an attempt to obtain an image minimized in distortions. The apparatus also comprises an aberroscope or aberrometer 80 and the data obtained by this device is passed to control system 50. Control system 50 may comprise a control system 51 for the data emanating from adaptive optics 30 and a control system 52 for the data emanating from aberrometer 80. The vision correcting data 55 generated by control system 50 may be utilized with laser treatment apparatus 60.

Figure 6:
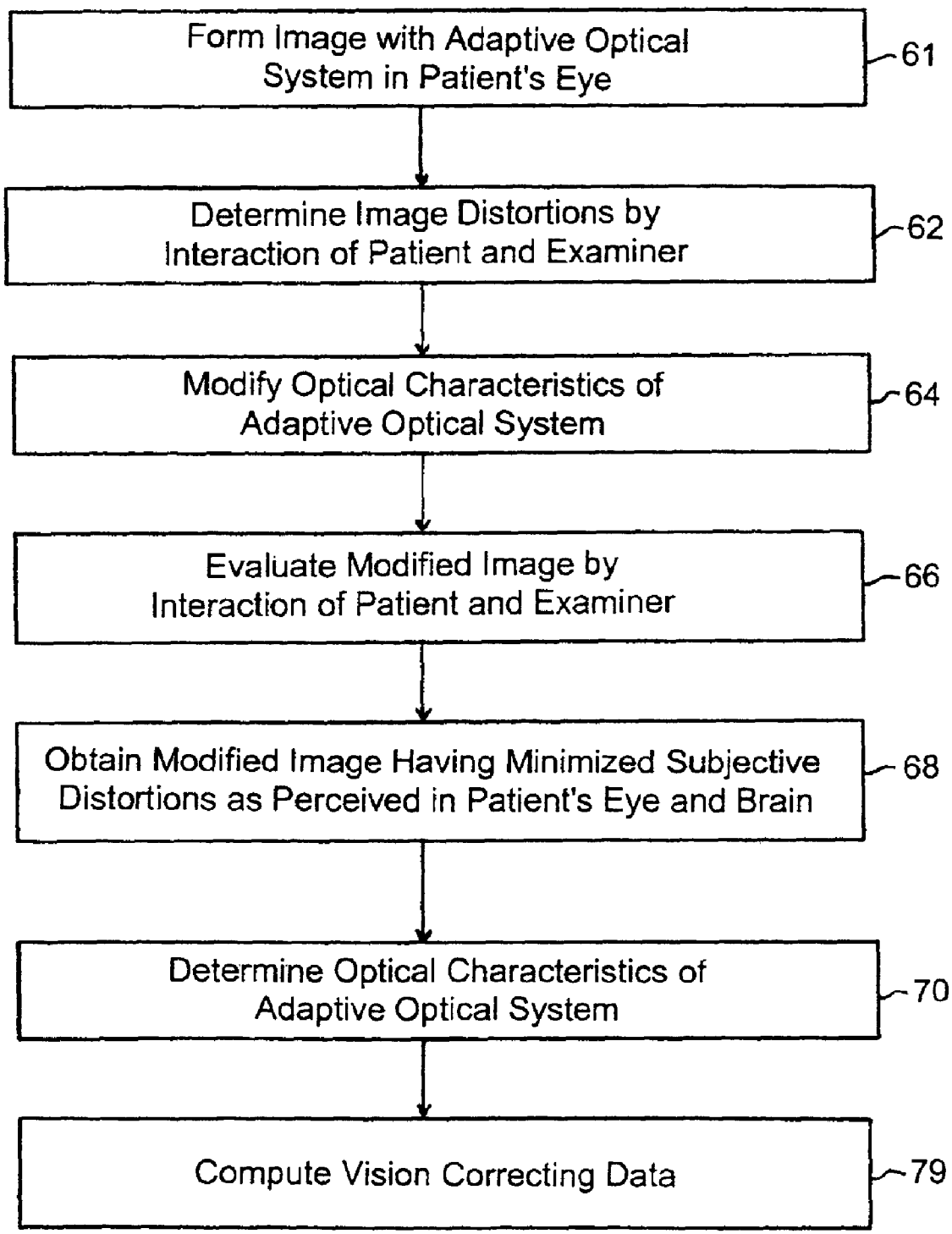
FIG. 6 is a flow diagram for examining and evaluating a test image.

FIG. 6 illustrates an embodiment of a method in accordance with at least one possible embodiment. Thus, in step 61 an image is formed with the adaptive optical system 30 in the eye 10 and brain of the patient. By interaction between the patient and the examiner image distortions are determined in step 62. This possibly leads to modification of the optical characteristics of the adaptive optical system 30 in step 64. The modified image, produced by changing the position of the micromirror devices or micromirrors 31 of the adaptive optical system 30, is evaluated, again by interaction between the examiner and the patient in step 66. The evaluations and image modifications are repeated until a modified image having minimized subjective distortions as perceived in the patients eye and brain has been obtained in step 68. Next, in step 70, the optical characteristics of the adaptive optical system 30, as modified, and in step 79 vision correcting data 55 are computed.

Figure 7:
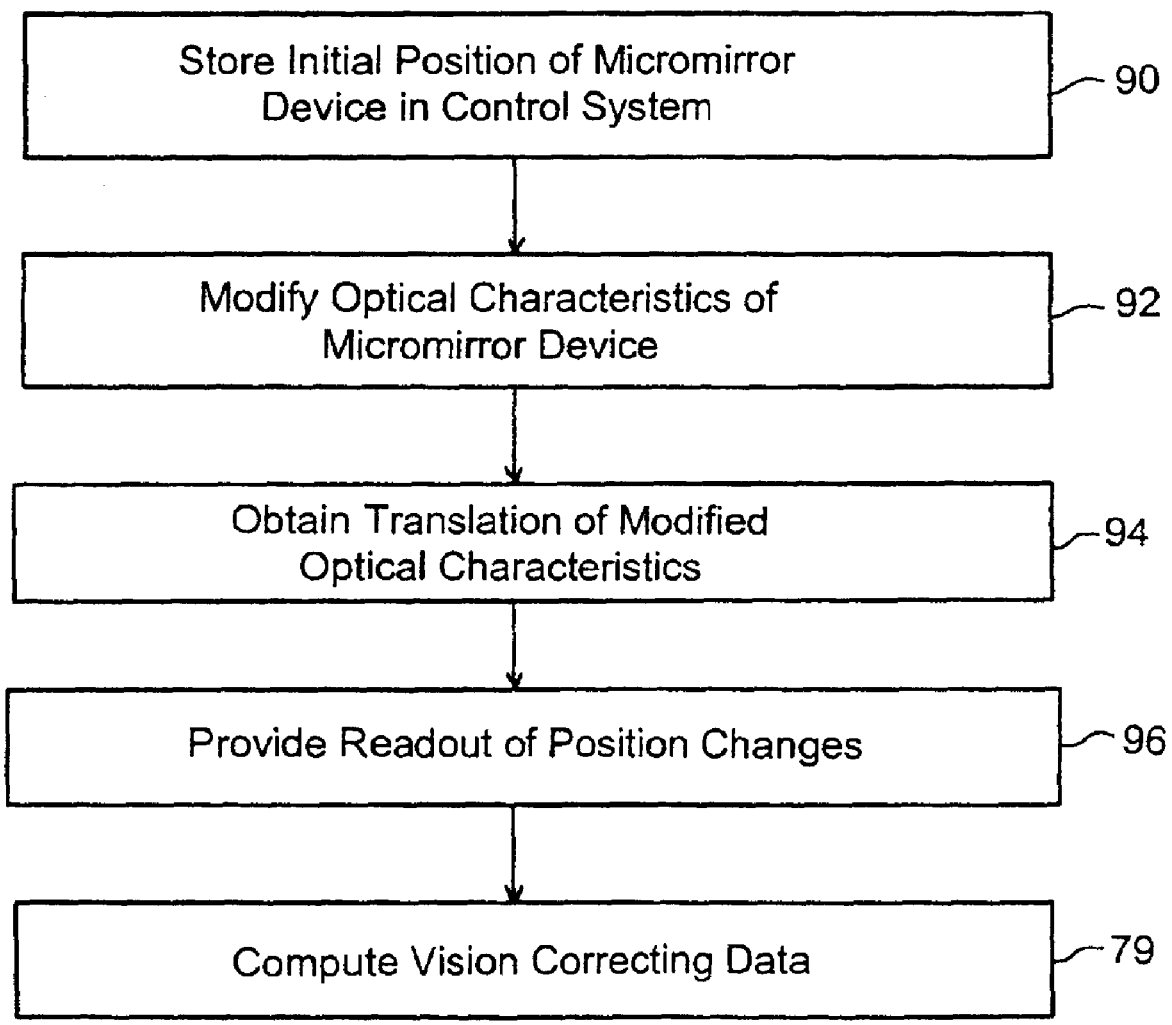
FIG. 7 is a flow diagram illustrating actuation of a micromirror and computation of vision correcting data.

FIG. 7 illustrates the steps representative of the modification of the optical characteristics of the micromirrors 31 of the adaptive optical system 30. Thus, in step 90 the initial position of the micromirrors, or micromirror devices, 31 is stored in the control system 50. The optical characteristics of the adaptive optical system 30, that is, the position of the individual micromirrors 31 is modified in step 92 to obtain an image that is minimized in distortion in the eye 10 of the patient. The modified optical characteristics of the micromirrors 31 are translated into suitable signals in step 94. The position changes of the micromirrors 31 may possibly be obtained through a read out, in step 96. Vision correcting data based on the modified positions of micromirrors may be accomplished in step 79, as mentioned above.

Figure 8:
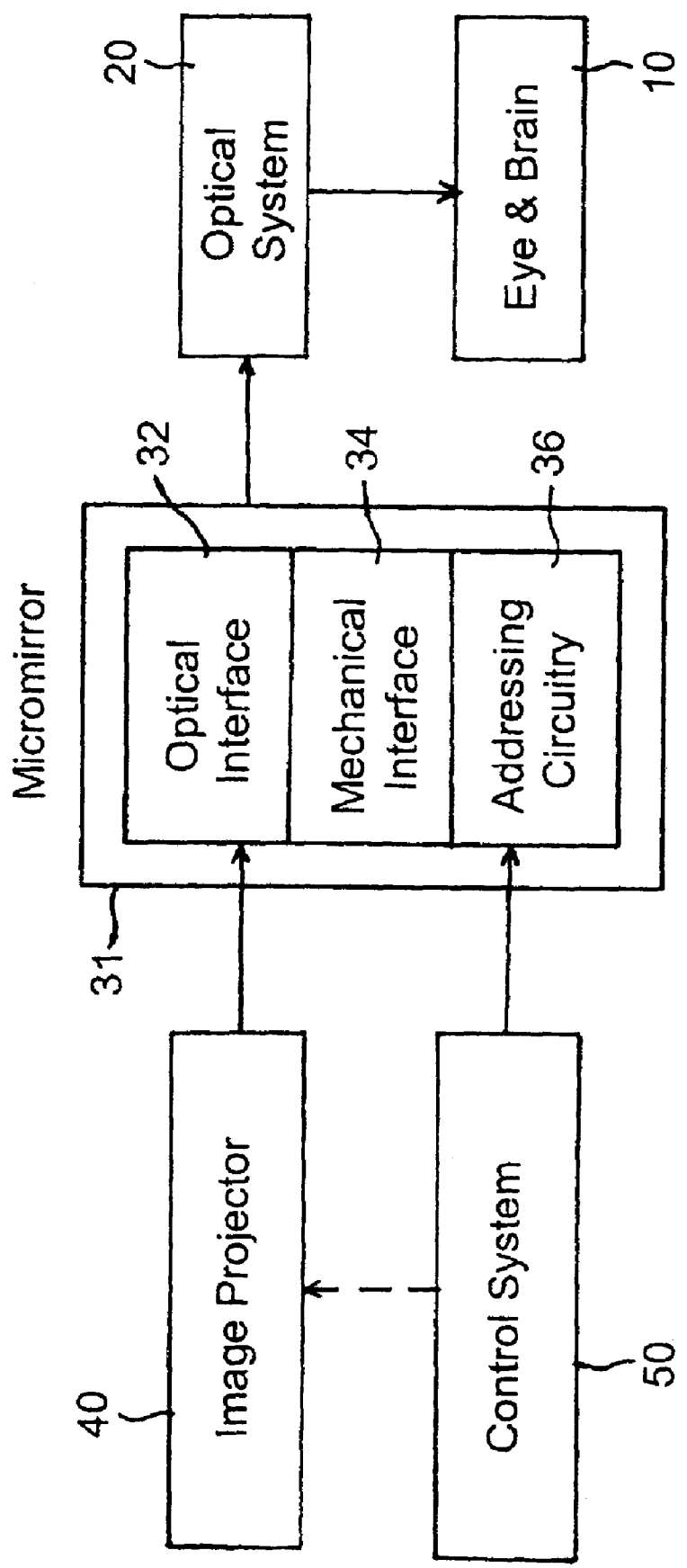
FIG. 8 illustrates a vision testing apparatus in accordance with at least one possible embodiment.

FIG. 8 illustrates an embodiment of an apparatus in accordance with the present invention, particularly illustrating the structure of a micromirror or micromirror device 31. Thus, the image projector 40 projects an image to the optical interface 32 of the micromirror 31. This image or portion is transmitted to optical system 20 and thence to the eye 10. The control system 50 is configured to provide signals to the addressing circuitry 36 of micromirror 31 to modify the optical characteristics of the optical interface 32 of micromirror 31, by way of a mechanical interface 34, such as, a membrane. Again, the modified image is projected from optical interface 32 of mirror 31 to the optical system 20 and from there to the eye 10 and brain of the patient.

Figure 9:
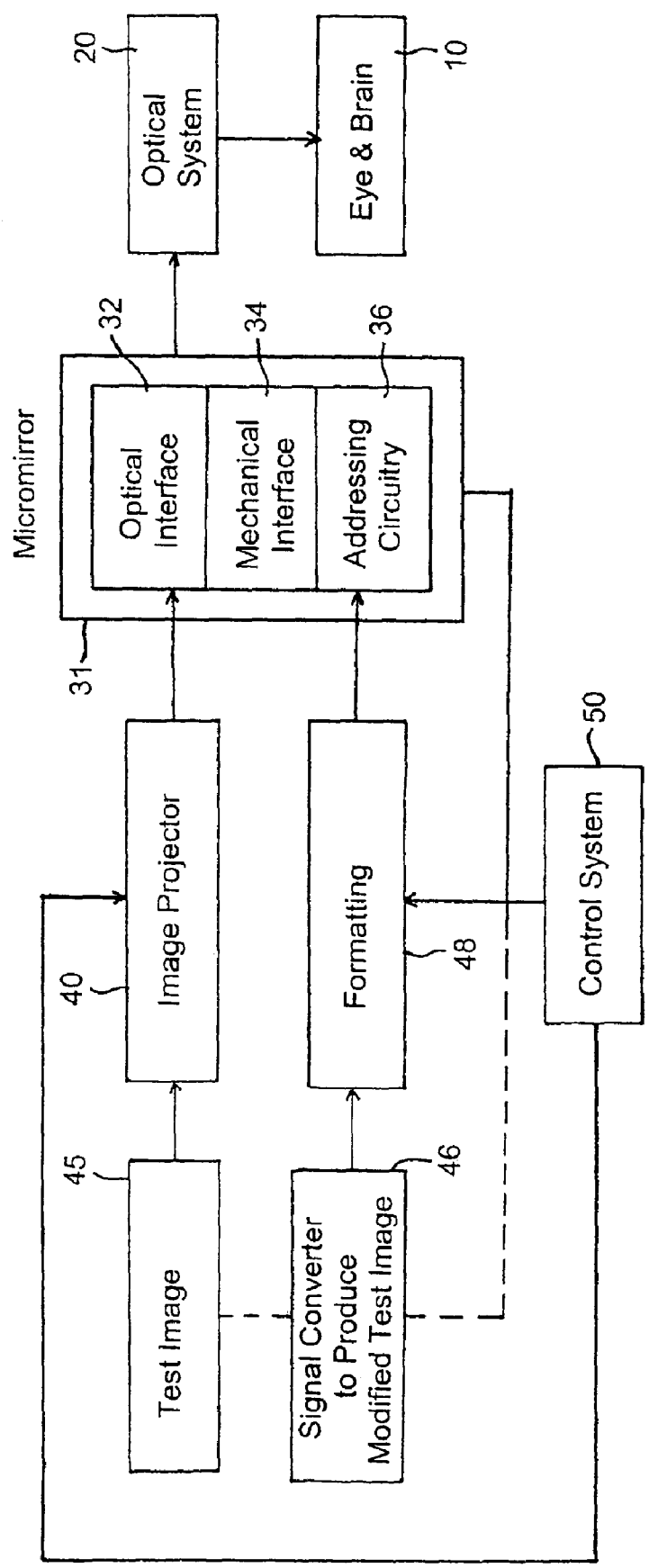
FIG. 9 illustrates a further embodiment of an apparatus in accordance with at least one possible embodiment.

FIG. 9 illustrates a further embodiment of an apparatus in accordance with the present invention. Test image 45 is projected by projector 40, possibly under the instructions from control system 50, onto the optical interface 32 of micromirror 31 and from there the image or portion is passed to the optical system 20 and the eye 10. Modifications of the image 45 may be effectuated by signal converter 46 in response to signals from control system 50. Thus, for example, spherical lens correction is possibly performed first by a pattern generated by modifications of the image attended to by the signal converter 46 in response to signals from the control system 50. Secondly, astigmatism is corrected in an analogous manner by the signal converter 46 passing input to formatting stage 48 in conformity with instructions from the control system 50. Subsequently, the higher-order distortions or aberrations can be corrected one after another by modifying the signals of the signal converter 46 by the control system 50. The output from signal converter 46 may be passed to formatter 48 and thence to the addressing circuitry 36 of micromirror 31. By way of the mechanical interface 34 the optical characteristics of optical interface 32 is changed to provide a modified image in eye 10 and brain of the patient. In at least one embodiment, the mechanical interface 34 may possibly comprise a membrane element actuated by an electrostatic arrangement, or a piezo-electric arrangement, or a bimorph membrane arrangement or the like device.

Figure 10:
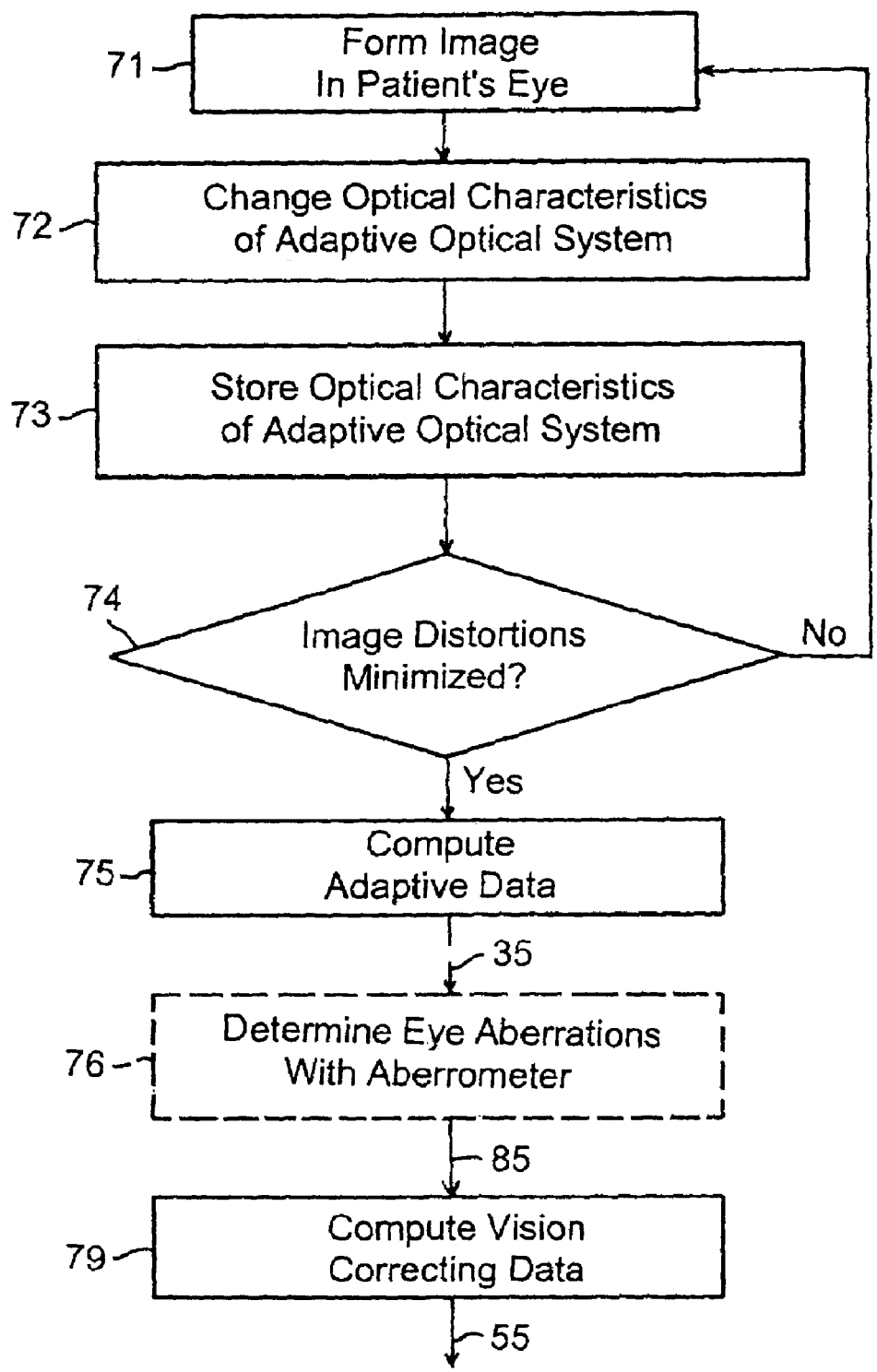
FIG. 10 is a flow diagram similar to FIG. 3 showing additional details.

FIG. 10 illustrates in greater detail the steps for obtaining vision correcting data. Thus in step 71 an image is formed in the eye of the patient. In step 72 the optical characteristics of the adaptive optical system 30 are changed in conformity with the interaction between the patient and the examiner. Step 73 comprises the storing of the optical characteristics of the adaptive optical system 30. An inquiry 74 leads to repetition of steps 72 and 73 in the event that distortions are substantially present. In the event that an image having minimized distortions has been obtained through interaction between the patient and the examiner, adaptive data are computed in step 75. In addition to the foregoing procedure, an aberrometer 80 may be employed in step 76 to determine eye aberrations and the corresponding data may be utilized in step 79 comprising computation of vision correcting data.

Figure 10A:
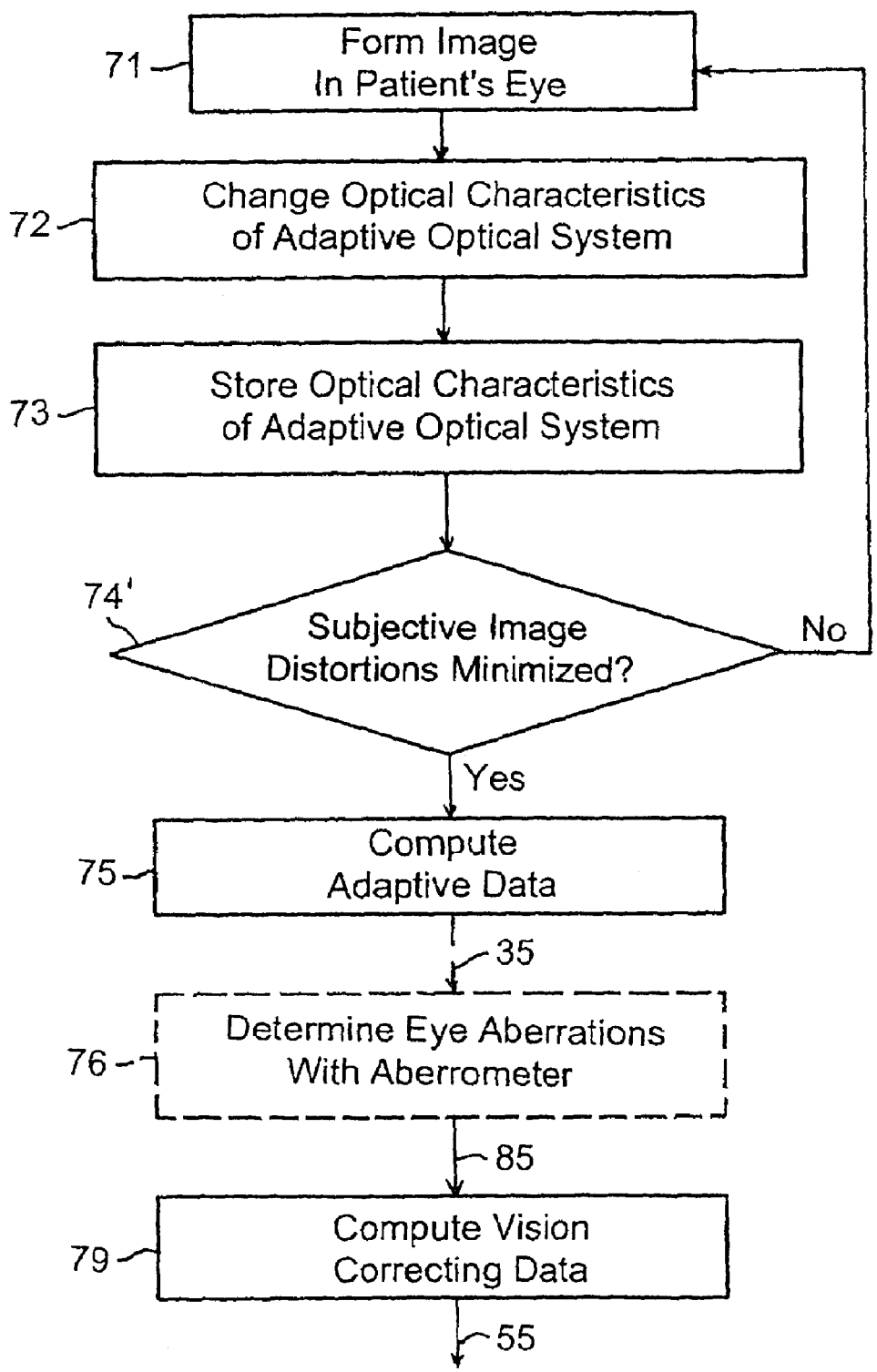
FIGS. 10a & 10b are flow diagrams similar to FIG. 10.

FIG. 10a is a flow diagram similar to FIG. 10 and in particular points out that an inquiry 74' addresses whether subjective image distortions have been minimized or not.

Figure 10B:
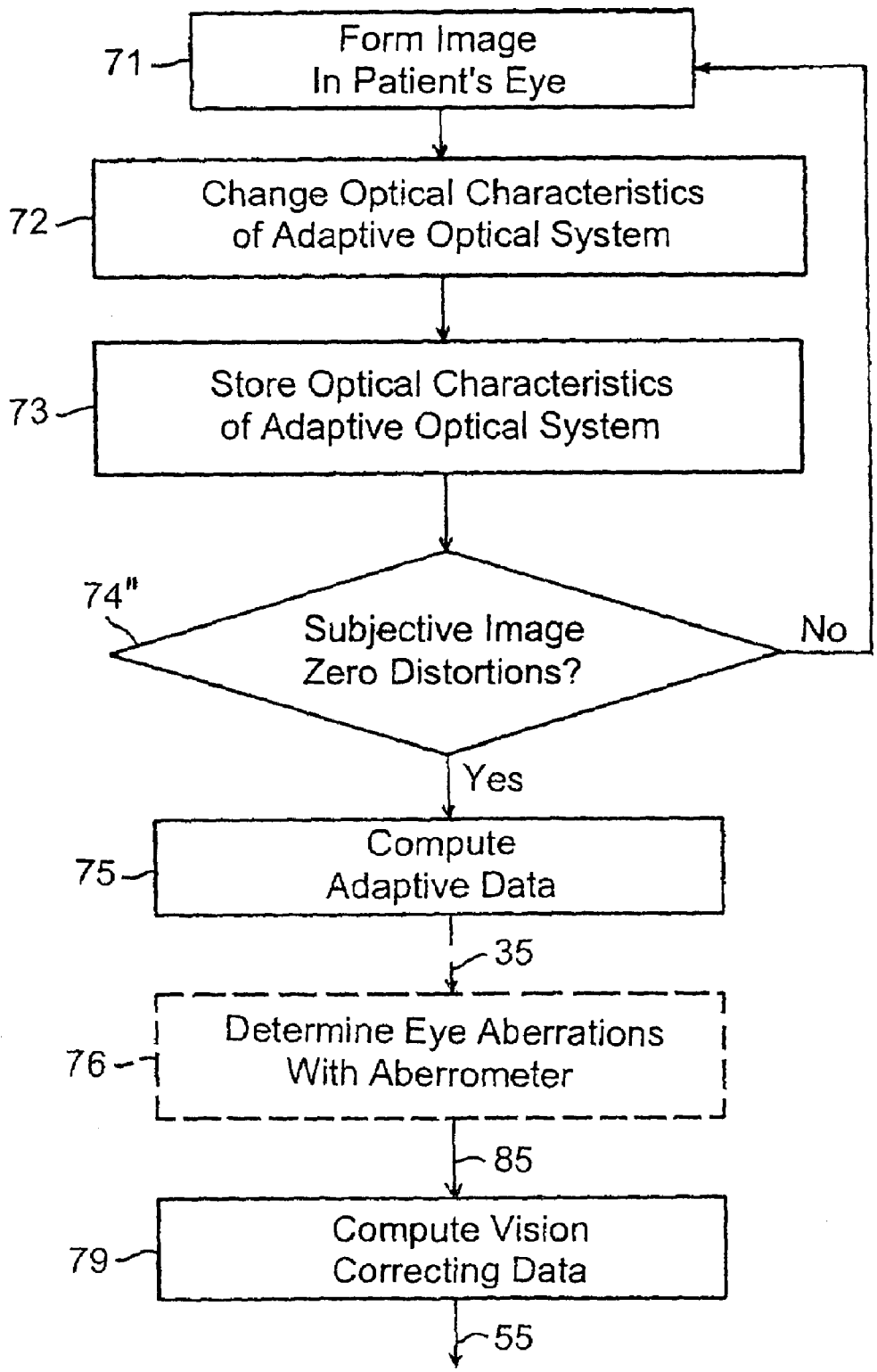
Figure 13:
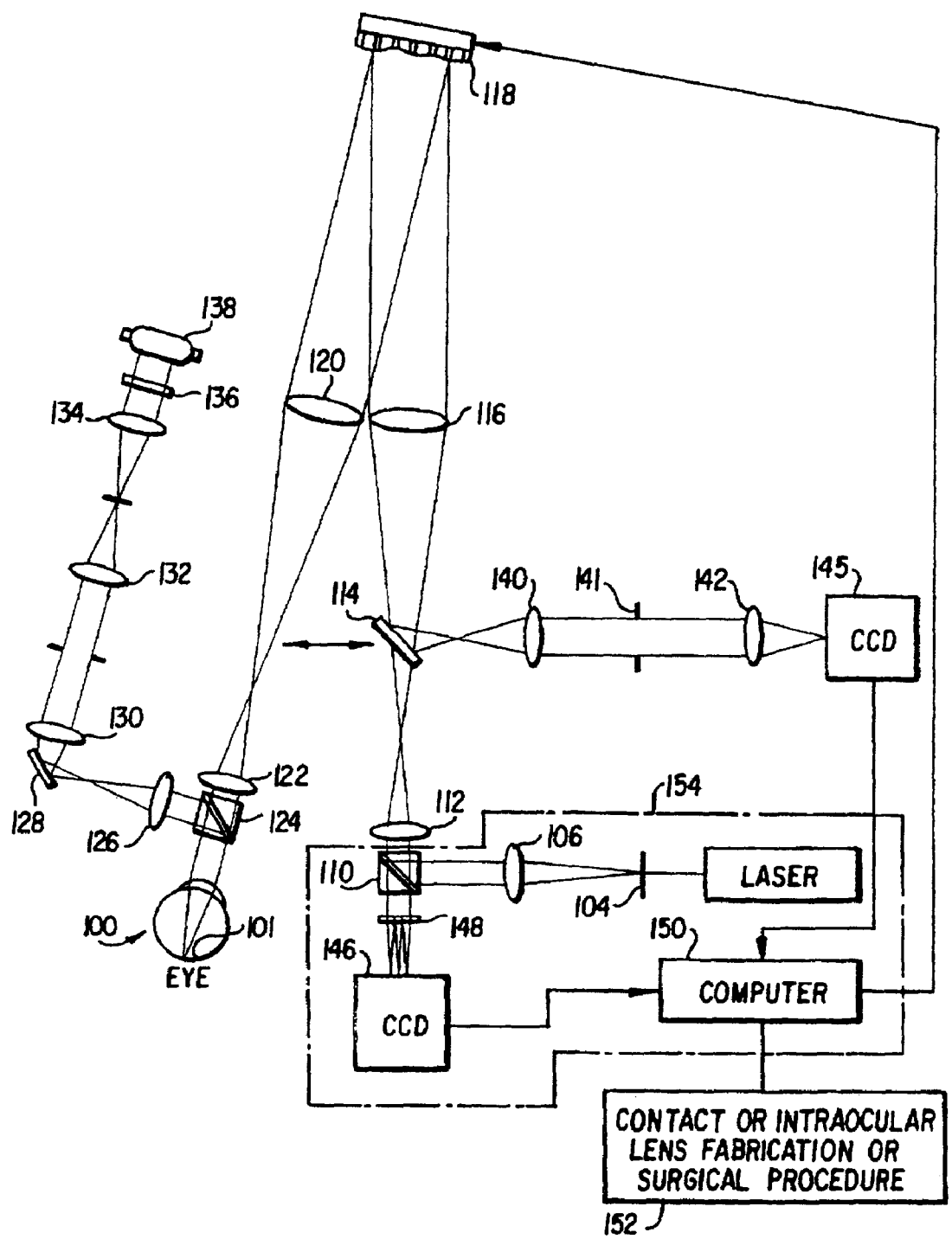
FIG. 13 is a block circuit diagram of an embodiment of an apparatus in accordance with still another aspect of the invention.

FIG. 10b is a flow diagram similar to FIG. 10 and particularly illustrates that inquiry 74" can lead to the result that subjective image distortions can be brought to substantially zero subjective image distortions.

FIG. 11 is a view similar to FIG. 2a and identifying a portion of a micromirror device with micromirrors 31.

FIG. 12 is a view similar to FIG. 2b and identifying an interface or membrane actuator element 34 that may possibly be actuated by electrostatic force, piezoelectric force, or bimorph force.

The present invention provides, accordingly, in accordance with one aspect, a method, and in accordance with a further aspect, an apparatus, for determining correcting data for the correction of eye aberrations, which does not solely take into consideration the aberrations of the optical display apparatus, but also take into consideration the characteristics of the receiving person and the signal processing in the human brain. A particular advantage resides therein that the correction data for display errors that negatively impact the faculty of vision are obtained in an a priori actively physiologically evaluated metrological method.

Although the human eye is an optical marvel, it suffers many deviations from being an ideal optical system, namely, aberrations. These may be grouped into lower-order aberrations and higher-order aberrations. Lower-order aberrations comprise basic refractive errors: myopia, hypermetropia and astigmatism. These may be treated by routine laser treatments. Higher-order aberrations possibly comprise: spherical aberration; chromatic aberration; coma; distortions: positive or pin-cushion distortions and negative or barrel-distortions; and Petzvald field curvature aberrations. Whereas the lower-order aberrations may be easily corrected leading the improvement of visual acuity, the higher-order aberrations do not lend themselves to easy solutions. Thus, the higher-order aberrations limit the potential visual acuity of the eye and they constitute about 17% of the total aberration error.

In at least one possible embodiment the patient may possibly change the image to minimize distortions as perceived in the eye using an input device, such as, a joystick, a touch pad, or a touch screen. It will be appreciated that the touch pad or touch screen may possibly be of the type that allows varying of the test image quality by applying more or less pressure to the region of the test image that the patient wishes to adjust. The applied pressure can then be translated into signals for a possible control system to compute vision correcting data.

It is also within the scope of at least one possible embodiment to utilize a cathode ray tube device to form an image in the eye of the patient and to modify the image to obtain an image with minimized distortions in the eye being examined.

In at least one possible embodiment, sets of different images may be stored in a computer by way of software and the image presenting minimized distortions may be selected by the patient from the stored set of images.

Computation of the adaptive data may, in at least one possible embodiment, be carried out using Zernike and/or Taylor polynomials. Such adaptive data can then be utilized to compute vision correcting data. Vision correcting data may possibly comprise data for determining the direction of a laser beam in laser treatment of vision defects.

Thus, at least one possible embodiment relates in one aspect to a metrological system for the active and physiologically rated investigation of substantially all aberrations of the human eye, with the metrological data serving as the basis to accomplish an optimal correction, particularly a laser correction, of the aberrations of the eye to thereby achieve a best possible faculty of vision for the human eye.

One feature of at least one possible embodiment resides broadly in the apparatus 1 for the determination of correction data 55 for the correction of aberrations of an eye 10 of a patient, comprising an optics system 20 characterized thereby that the apparatus 1 further comprises: an adaptive optics 30; an arrangement 40 for the display of test images by way of the adaptive optics 30; and a control system 50.

Another feature of at least one possible embodiment resides broadly in the apparatus 1 characterized thereby that the adaptive optics 30 is configured by a plurality of mirrors 31 that can be individually varied as to position.

Yet another feature of at least one possible embodiment resides broadly in the apparatus 1 characterized thereby that the adaptive optics 30 has the configuration of a segment of a sphere.

Still another feature of at least one possible embodiment resides broadly in the apparatus 1 characterized thereby that the adaptive optics 30 can be adjusted by means of a first control system 51.

A further feature of at least one possible embodiment resides broadly in the apparatus 1 characterized thereby that the apparatus 1 further comprises: an aberrations measuring system 80 for the determination of aberrations data 85 which correspond to the objective aberrations of the eye 10.

Another feature of at least one possible embodiment resides broadly in the apparatus 1 characterized thereby that the correction data 55 for the correction of the aberrations of the eye 10 can be determined by a second control system 52 on the basis of adaptive data 35 corresponding to the adaptive optics 30, or on the basis of the adaptive data 35 and the aberrations data 85.

Yet another feature of at least one possible embodiment resides broadly in the method for the determination of correction data 55 for the correction of aberrations of an eye 10 characterized thereby that in a first step 73 are determined, by means of an adaptive optics 30, adaptive data 35 corresponding to a subjectively optimal correction adjustment of the eye 10 and in a further step 79 are determined the correction data 55 for the correction of the eye 10 which correction data are based on the adaptive data 35.

Still another feature of at least one possible embodiment resides broadly in the method characterized thereby that additionally aberration data 85 are determined which correspond to the objective aberrations of the eye 10 and the correction data 55 are determined on the basis of the adaptive data 35 and the aberration data 85.

A further feature of at least one possible embodiment resides broadly in the method characterized thereby that the adaptive data 35 corresponding to a subjectively optimal correction adjustment of the eye 10 are obtained by a subjective evaluation by the patient of modified test images 45 modified by varying the mirror position of the mirrors 31 of the adaptive optics 30.

Thus, this invention relates in one aspect to an apparatus, and in another aspect to a method, for the determination of correction data to correct aberrations of the eye.

The components disclosed in the various publications, disclosed or incorporated by reference herein, may be used in the embodiments of the present invention, as well as equivalents thereof.

The appended drawings in their entirety, including all dimensions, proportions and/or shapes in at least one embodiment of at least one possible embodiment, are accurate and are hereby included by reference into this specification.

All, or substantially all, of the components and methods of the various embodiments may be used with at least one embodiment or all of the embodiments, if more than one embodiment is described herein.

All of the patents, patent applications and publications recited herein, and in the Declaration attached hereto, are hereby incorporated by reference as if set forth in their entirety herein.

The following patents, patent applications, or patent publications and other publications, which were cited in the International Search Report in International Patent Application No. PCT/EP00/012116, dated Apr. 24, 2001, are hereby incorporated by reference as if set forth in their entirety herein as follows: International Patent Publication WO 93 22711 of Nov. 11, 1993 (corresponding to U.S. Pat. No. 5,142,132 issued to inventors MacDonald et al. on Aug. 25, 1992 and entitled "Adaptive optic wafer stepper illumination device"); and U.S. Pat. No. 4,579,430 issued to inventor Bille on Apr. 1, 1986 and entitled "Method and apparatus for forming an image of the ocular fundus."

The following references, also referred to above, are hereby incorporated by reference as if set forth in their entirety herein: P. Mierdel, H.-E. Krinke, W. Wiegand, M. Kaemmerer, T. Seiler, "*Meβplatz zur Bestimmung der monochromatischen Aberration des menschlichen Auges {Test station for the determination of the monochromatic aberration of the human eye}*", OPHTHALMOLOGE, 1997, 94; pages 441-445, SPRINGER VERLAG, 1997); LASER FOCUS WORLD, April 1999, pages 35-36; LASER FOCUS WORLD, August 1998, pages 18-22; and German Patent Publication No. 19 733 193 A1 (corresponding to International Patent Publication WO 99/06856 of Feb. 11, 1999, having inventors Simon et al. and having the title "Microscope with adaptive optics system").

The following references, which are cited in the International Examination Report are incorporated by reference as follows: Liang et al: "*Supernormal vision and high-resolution retinal imaging through adaptive optics*", J. Opt. Soc. Am. A/Vol 14, No. 11/November 1997 and U.S. Pat. No. 5,777,719. Any references listed in the Preliminary Examination Report WO 01/39660 (German version of the First Examination Report WO 01/39660 are also incorporated by reference herein.

The following references, which are cited in Federal Republic of Germany Patent Application No. DE 199 58 436.2 are hereby incorporated by reference as if set forth in their entirety herein as follow: U.S. Pat. No. 5,805,119; U.S. Pat. No. 5,675,399; and Federal Republic of Germany Laid-open Patent Application No. 37 33 872.

The corresponding international patent publication application, namely, International Application No. PCT/EP2007/000388, filed on Jan. 17, 2007, published under number WO 2007/082736 on Jul. 26, 2007, having inventors Manfred click, Holger MÄUSEZAHL, and Eckhard SCHRÖDER, as well as its published equivalents, and other equivalents or corresponding applications, if any, in corresponding cases in Germany or elsewhere, and the references and documents cited in any of the documents cited therein, such as the patents, patent applications and publications, are hereby incorporated by reference as if set forth in their entirety herein.

The following foreign and international patent publication applications, namely, International Application No. PCT/EP00/12116, filed on Dec. 1, 2000, published under number WO 01/39660 on Jun. 7, 2001, and claiming priority from Federal Republic of Germany Patent Application No. DE 199 58 436.2, filed on Dec. 3, 1999, both having inventors Manfred click, Holger MÄUSEZAHL, and Eckhard SCHRÖDER, and having the title "DEVICE AND METHOD FOR DETERMINING THE CORRECTION DATA FOR CORRECTING ABERRATIONS OF THE EYE," as well as their published equivalents, and other equivalents or corresponding applications, if any, in corresponding cases in Germany and elsewhere, and the references and documents cited in any of the documents cited herein, such as the patents, patent applications and publications, are hereby incorporated by reference as if set forth in their entirety herein.

All of the references and documents, cited in any of the documents cited herein, and the references they are in turn cited in are hereby incorporated by reference as if set forth in their entirety herein. All of the documents cited herein, referred to in the immediately preceding sentence, include all of the patents, patent applications and publications cited anywhere in the present application. All of the references included herein as aforesaid include the corresponding equivalents published by the United States Patent and Trademark Office and elsewhere.

Some examples of measuring or examining aberrations of the eye, features of which may possibly be used or adapted for use in at least one possible embodiment may be found in the following U.S. Pat. No. 3,984,156 issued to inventor Jernigan on Oct. 5, 1976 and entitled "Objective plotting of visual fields by eye movement monitoring;" U.S. Pat. No. 4,641,962 issued to inventors Sueda et al. on Feb. 10, 1987 and entitled "Aberration measuring method;" U.S. Pat. No. 4,711,576 issued to inventor Ban on Dec. 8, 1987 and entitled "Wave front aberration measuring apparatus;" U.S. Pat. No. 5,062,702 issued to inventor Bille on Nov. 5, 1991 and entitled "Device for mapping corneal topography;" U.S. Pat. No. 5,157,459 issued to inventors Oono et al. on Oct. 20, 1992 and entitled "Wave front aberration measuring apparatus;" U.S. Pat. No. 5,307,097 issued to inventor Baker on Apr. 26, 1994 and entitled "Corneal topography system including single direction shearing of holograph grating in orthogonal directions;" U.S. Pat. No. 5,760,879 issued to inventors Shinonaga et al. on Jun. 2, 1998 and entitled "Method of detecting coma of projection optical system;" U.S. Pat. No. 5,777,719 issued to inventors Williams et al. on Jul. 7, 1998 and entitled "Method and apparatus for improving vision and the resolution of retinal images;" U.S. Pat. No. 5,805,273 issued to inventor Unno on Sep. 8, 1998 and entitled "Projection exposure apparatus and microdevice manufacturing method;" U.S. Pat. No. 5,898,501 issued to inventors Suzuki et al. on Apr. 27, 1999 and entitled "Apparatus and methods for measuring wavefront aberrations of a microlithography projection lens;" U.S. Pat. No. 5,943,117 issued to inventor Van de Velde on Aug. 24, 1999 and entitled "Scanning laser opthalmoscope for retinal microphotocoagulation and measurement of wavefront aberrations;" U.S. Pat. No. 6,002,484 issued to inventors Rozema et al. on Dec. 14, 1999 and entitled "Phase contrast aberroscope;" U.S. Pat. No. 6,008,781 issued to inventors Furness, III et al. on Dec. 28, 1999 and entitled "Virtual retinal display;" U.S. Pat. No. 6,008,904 issued to inventors Ishii et al. on Dec. 28, 1999 and entitled "Apparatus and methods for detecting and correcting distortion of interference fringes;" U.S. Pat. No. 6,042,233 issued to inventors Mihashi et al. on Mar. 28, 2000 and entitled "Optical characteristic measuring apparatus;" U.S. Pat. No. 6,086,204 issued to inventor Magnante on Jul. 11, 2000 and entitled "Methods and devices to design and fabricate surfaces on contact lenses and on corneal tissue that correct the eye's optical aberrations;" U.S. Pat. No. 6,199,986 issued to inventors Williams et al. on Mar. 13, 2001 and entitled "Rapid, automatic measurement of the eye's wave aberration;" U.S. Pat. No. 6,220,707 issued to inventor Bille on Apr. 24, 2001 and entitled "Method for programming an active mirror to mimic a wavefront;" U.S. Pat. No. 6,234,631 issued to inventors Sarver et al. on May 22, 2001 and entitled "Combination advanced corneal topography/wave front aberration measurement;" U.S. Pat. No. 6,264,328 issued to inventors Williams et al. on Jul. 24, 2001 and entitled "Wavefront sensor with off-axis illumination;" U.S. Pat. No. 6,270,221 issued to inventors Liang et al. on Aug. 7, 2001 and entitled "Apparatus and method for measuring vision defects of a human eye;" U.S. Pat. No. 6,271,914 issued to inventors Frey et al. on Aug. 7, 2001 and entitled "Objective measurement and correction of optical systems using wavefront analysis;" U.S. Pat. No. 6,276,800 issued to inventor Baker on Aug. 21, 2001 and entitled "System for modeling a wavefront using sheared phase shifts;" U.S. Pat. No. 6,281,805 issued to inventor Lee on Aug. 28, 2001 and entitled "Automotive CCD camera;" U.S. Pat. No. 6,286,959 issued to inventor Otten on Sep. 11, 2001 and entitled "Wavefront characterization of corneas;" U.S. Pat. No. 6,299,311 issued to inventors Williams et al. on Oct. 9, 2001 and entitled "Rapid, automatic measurement of the eye's wave aberration;" U.S. Pat. No. 6,313,951 issued to inventors Manhart et al. on Nov. 6, 2001 and entitled "Optical system with Zernike-shared corrector;" and U.S. Pat. No. 6,331,059 issued to inventors Kudryashov et al. on Dec. 18, 2001 and entitled "High resolution multispectral, wide field of view retinal imager." All of the foregoing patents are hereby expressly incorporated by reference as if fully set forth in their entirety herein.

The following information relating to the WASCA analyzer, an aberrometer device, available from website http://www.asclepion.com/english/laserpost/19/product_news.php is hereby incorporated by reference as if set forth in its entirety herein.

International Patent Application WO 01/12113 published on Feb. 22, 2001 having inventors Dick et al. and having the title "Method and device for performing online aberrometrie in refractive eye correction indices;" and International Patent Application WO 01/12114 published on Feb. 22, 2001 having inventors Dick et al and having the title "Method and device for completely correcting visual defects of the human eye." Both international patent applications are assigned to ASCLEPION MEDITEC AG. These two patent publications are hereby expressly incorporated by reference as if fully set forth in their entirety herein.

Some examples of adaptive optics methods and apparatus, features of which may possibly be used or adapted for use in at least one embodiment of the present invention may be found in the following U.S. Pat. No. 4,271,355 issued to inventors Wisner et al. on Jun. 2, 1981 and entitled "Method for mitigating $2\pi N$ ambiguity in an adaptive optics control system;" U.S. Pat. No. 4,295,741 issued to inventors Palma et al. on Oct. 20, 1981 and entitled "Two-wavelength phase control system;" U.S. Pat. No. 4,547,662 issued to inventor Cornwell on Oct. 15, 1985 and entitled "Noninterference optical error sensing system;" U.S. Pat. No. 4,666,298 issued to inventor Protz on May 19, 1987 and entitled "Sensing device for ascertaining imaging errors;" U.S. Pat. No. 4,750,818 issued to inventor Cochran on Jun. 14, 1988 and entitled "Phase conjugation method;" U.S. Pat. No. 4,950,878 issued to inventors Ulich et al. on Aug. 21, 1990 and entitled "Wavefront control system using optical coarse/fine gradient sensor;" U.S. Pat. No. 4,967,063 issued to inventors Wang et al. on Oct. 30, 1990 and entitled "Charge controlled adaptive-optics system;" U.S. Pat. No. 4,996,412 issued to inventors Anafi et al. on Feb. 26, 1991 and entitled "Optical system for wavefront compensation;" U.S. Pat. No. 5,076,670 issued to inventor Sayyah on Dec. 31, 1991 and entitled "Isolated pixel liquid crystal light valve structure;" U.S. Pat. No. 5,091,801 issued to inventor Ebstein on Feb. 25, 1992 and entitled "Method and apparatus for adjusting the focal length of an optical system;" U.S. Pat. No. 5,111,125 issued to inventor Barrs on May 5, 1992 and entitled "Automatic mirror repositioning;" U.S. Pat. No. 5,137,354 issued to inventors deVos et al. on Aug. 11, 1992 and entitled "Computer aided three dimensional positioning sensing system and method;" U.S. Pat. No. 5,151,814 issued to inventors Grinberg et al. on Sep. 29, 1992 and entitled "Phased array for optical beam control;" U.S. Pat. No. 5,194,789 issued to inventor Barrs on Mar. 16, 1993 and entitled "Automatic mirror repositioning system diagnostics;" U.S. Pat. No. 5,245,562 issued to inventor Dettmer on Sep. 14, 1993 and entitled "Accumulating arithmetic memory integrated circuit;" U.S. Pat. No. 5,287,165 issued to inventors Ulich et al. on Feb. 15, 1994 and entitled "High sensitivity-wide dynamic range optical tile sensor;" U.S. Pat. No. 5,396,364 issued to inventors O'Meara et al. on Mar. 7, 1995 and entitled "A continuously operated spatial light modulator apparatus and method for adaptive optics;" U.S. Pat. No. 5,684,545 issued to inventors Dou et al. on Nov. 4, 1997 and entitled "Adaptive optics wave measurement and correction system;" U.S. Pat. No. 5,745,309 issued to inventor Salmon on Apr. 28, 1998 and entitled "Method for removing tilt control in adaptive optics systems;" U.S. Pat. No. 6,038,058 issued to inventors Robinson et al. on Mar. 14, 2000 and entitled "Grid-actuated charge controlled mirror and method of addressing the same;" U.S. Pat. No. 6,155,684 issued to inventors Bille et al. on Dec. 5, 2000 and entitled "Method and apparatus for precompensating the refractive properties of the human eye with adaptive optical feedback control;" U.S. Pat. No. 6,057,913 issued to inventors Brown et al. on May 2, 2000 and entitled "Compact shearing wavefront sensor and apparatus" and U.S. Pat. No. 6,338,559 issued to inventors Williams et al. on Jan. 15, 2002 and entitled "Apparatus and method for improving vision and retinal imaging." All of the foregoing patents are hereby expressly incorporated by reference as if fully set forth in their entirety herein.

Some examples of micromirrors and actuation thereof, features of which may possibly be used or adapted for use in at least one embodiment of the present invention may be found in the following U.S. Pat. No. 5,109,349 issued to inventors Ulich et al. on Apr. 28, 1992 and entitled "Actively controlled segmented mirror;" U.S. Pat. No. 5,448,395 issued to inventors Lopez et al. on Sep. 5, 1995 and entitled "Non-mechanical step-scanner for electro-optical sensors;" U.S. Pat. No. 5,493,391 issued to inventors Neal et al. on Feb. 20, 1996 and entitled "One dimensional wavefront distortion sensor comprising a lens array system;" U.S. Pat. No. 5,572,543 issued to inventors Heinemann et al. on Nov. 5, 1996 and entitled "Laser system with a micro-mechanically moved mirror;" U.S. Pat. No. 5,612,713 issued to inventors Bhuva et al. on Mar. 18, 1997 and entitled "Digital micromirror device with block data logging;" U.S. Pat. No. 5,737,075 issued to inventors Koch et al. on Apr. 7, 1998 and entitled "Electronic imaging by encoded image detection;" U.S. Pat. No. 5,818,627 issued to inventors Perlo et al. on Oct. 6, 1998 and entitled "Devices with micro-mirrors and micro-filters for selecting colors and images;" U.S. Pat. No. 5,926,309 issued to inventor Little on Jul. 20, 1999 and entitled "Light valve target comprising electrostatically-repelled micro-mirrors;" U.S. Pat. No. 6,046,808 issued to inventor Fateley on Apr. 4, 2000 and entitled "Radiation filter, spectrometer and imager using a micro-mirror array;" U.S. Pat. No. 6,046,840 issued to inventor Huibers on Apr. 4, 2000 and entitled "Double substrate reflective spatial light modulator with self-limiting micro-mechanical elements;" U.S. Pat. No. 6,064,366 issued to inventors Millward et al. on May 16, 2000 and entitled, "Spatial light modulators;" U.S. Pat. No. 6,097,859 issued to inventors Solgaard et al. on Aug. 1, 2000 and entitled "Multi-wavelength cross-connect optical switch;" U.S. Pat. No. 6,128,078 issued to inventor Fateley on Oct. 3, 2000 and entitled "Radiation filter spectrometer and imager using a micro-mirror array;" U.S. Pat. No. 6,181,460 issued to inventors Tran et al. on Jan. 30, 2001 and entitled "Electromagnetic force controlled micromirror array;" U.S. Pat. No. 6,259,548 issued to inventors Tsugai et al. on Jul. 10, 2001 and entitled "Micro-mirror device;" U.S. Pat. No. 6,263,123 issued to inventors Bishop et al. on Jul. 17, 2001 and entitled "Pixellated WDM optical components;" U.S. Pat. No. 6,271,958 issued to inventors Lin et al. on Aug. 7, 2001 and entitled "Method and apparatus for curvature resistant micro-mirror structures to reduce light beam loss in free-space micromachined optical switches;" U.S. Pat. No. 6,293,680 issued to inventor Bruns on Sep. 25, 2001 and entitled "Electromagnetically controlled deformable mirror;" U.S. Pat. No. 6,307,452 issued to inventor Sun on Oct. 23, 2001 and entitled "Folded spring based micro electromechanical (MEM) RF switch;" U.S. Pat. No. 6,307,681 issued to inventors Aoki et al. on Oct. 23, 2001 and entitled "Electro-optical device, electronic equipment, and method of driving an electro-optical device;" U.S. Pat. No. 6,323,834 issued to inventors Colgan et al. on Nov. 27, 2001 and entitled "Micromechanical displays and fabrication method;" U.S. Pat. No. 6,327,398 issued to inventors Solgaard et al. on Dec. 4, 2001 and entitled "Multi-wavelength cross connect optical switch;" U.S. Pat. No. 6,359,718 issued to inventors Lin et al. on Mar. 19, 2002 and entitled "Actuating mechanism for rotating a micromirror;" U.S. Pat. No. 6,360,036 issued to inventor Couillard on Mar. 19, 2002 and entitled "MEMS optical switch and method of manufacture;" and U.S. Pat. No. 6,362,556 issued to inventor Hoen on Mar. 26, 2002 and entitled "Electrically activated optical switch having a surface pivotable mirror." All of the foregoing patents are hereby expressly incorporated by reference as if fully set forth in their entirety herein.

The literature concerning the scanning two axis tilt mirror available from MEMS Optical Inc., 205 Import Circle, Huntsville, Ala. 35806 is hereby incorporated by reference as if set forth in its entirety herein. Such literature information on such mirror is available from website http://memsoptical.com/prodserv/products/twotiltmir.htm.

The literature concerning moving mirrors for tunable lasers available from MEMS Optical Inc., 205 Import Circle, Huntsville, Ala. 35806 is hereby incorporated by reference as if set forth in its entirety herein. Such literature information on such mirror is available from website http://memsoptical.com/prodserv/products/mov_mirror.htm.

The literature concerning the continuous membrane deformable mirror available from MEMS Optical Inc., 205 Import Circle, Huntsville, Ala. 35806 is hereby incorporated by reference as if set forth in its entirety herein. Such literature information on such mirror is available from website http://memsoptical.com/prodserv/products/def_mirrors.

Some examples of digital micromirror devices (DMD) and methods of actuating micromirror devices, features of which may possibly be used or adapted for use in at least one possible embodiment may be found in the following U.S. Pat. No. 5,099,353 issued to inventor Hornbeck on Mar. 24, 1992 and entitled "Architecture and process for integrating DMD switch control circuit substrates;" U.S. Pat. No. 5,142,405 issued to inventor Hornbeck on Aug. 25, 1992 and entitled "Bistable DMD addressing circuit and method;" U.S. Pat. No. 5,170,156 issued to inventors DeMond et al. on Dec. 8, 1992 and entitled "Multi-frequency two dimensional display system;" U.S. Pat. No. 5,214,419 issued to inventors DeMond et al. on May 25, 1993 and entitled "Planarized true three dimensional display;" U.S. Pat. No. 5,280,277 issued to inventor Hornbeck on Jan. 18, 1994 and entitled "Field updated deformable mirror device;" U.S. Pat. No. 5,285,196 issued to inventor Gale, Jr. on Feb. 8, 1994 and entitled "Bistable DMD addressing method;" U.S. Pat. No. 5,382,961 issued to inventor Gale, Jr. on Jan. 17, 1995 and entitled "Bistable DMD addressing method;" U.S. Pat. No. 5,506,597 issued to inventors Thompson et al. on Apr. 9, 1996 and entitled "Apparatus and method for image projection;" U.S. Pat. No. 5,526,172 issued to inventor Kanack on Jun. 11, 1996 and entitled "Microminiature, monolithic, variable electrical signal processor and apparatus including same;" U.S. Pat. No. 5,583,688 issued to inventor Hornbeck on Dec. 10, 1996 and entitled "Multi-level digital micromirror device;" U.S. Pat. No. 5,589,852 issued to inventors Thompson et al. on Dec. 31, 1996 and entitled "Apparatus and method for image projection with pixel intensity control;" U.S. Pat. No. 5,600,383 issued to inventor Hornbeck on Feb. 4, 1997 and entitled "Multi-level deformable mirror device with torsion hinges placed in a layer different from the torsion beam layer;" U.S. Pat. No. 5,633,691 issued to inventors Vogeley et al. on May 27, 1997 and entitled "Stylus position sensing and digital camera with a digital micromirror device;" U.S. Pat. No. 5,670,976 issued to inventors Chiu et al. on Sep. 23, 1997 and entitled "Spatial light modulator having redundant memory cells;" U.S. Pat. No. 5,686,939 issued to inventors Millward et al. on Nov. 11, 1997 and entitled "Spatial light modulators;" U.S. Pat. No. 5,768,007 issued to inventors Knipe et al. on Jun. 16, 1998 and entitled "Phase matched reset for digital micro mirror device;" U.S. Pat. No. 6,064,366 issued to inventors Millward et al. on May 16, 2000 and entitled "Spatial light modulators;" U.S. Pat. No. 6,064,398 issued to inventors Ellenby et al. on May 16, 2000 and entitled "Electro-optic vision systems;" U.S. Pat. No. 6,137,941 issued to inventor Robinson on Oct. 24, 2000 and entitled "Variable optical attenuator;" U.S. Pat. No. 6,157,396 issued to inventors Margulis et al. on Dec. 5, 2000 and entitled "System and method for using bitstream information to process images for use in digital display systems;" U.S. Pat. No. 6,184,852 issued to inventors Millward et al. on Feb. 6, 2001 and entitled "Spatial light modulators;" U.S. Pat. No. 6,191,883 issued to inventors Huffman et al. on Feb. 20, 2001 and entitled "Five transistor SRAM cell for small micromirror elements;" U.S. Pat. No. 6,208,318 issued to inventors Anderson et al. on Mar. 27, 2001 and entitled "System and method for high resolution volume display using a planar array;" U.S. Pat. No. 6,232,936 issued to inventors Gove et al. on May 15, 2001 and entitled "DMD architecture to improve horizontal resolution;" U.S. Pat. No. 6,259,450 issued to inventors Chiabrera et al. on Jul. 10, 2001 and entitled "Three-dimensional display system, apparatus and method;" and U.S. Pat. No. 6,310,588 issued to inventors Kawahara et al. on Oct. 30, 2001 and entitled "Image display apparatus and image evaluation apparatus." All of the foregoing patents are hereby expressly incorporated by reference as if fully set forth in their entirety here.

Some examples of membrane actuated modulators and methods of actuating modulators, features of which may possibly be used or adapted for use in at least one possible embodiment may be found in the following U.S. Pat. No. 4,746,791 issued to inventor Forkel on May 24, 1988 and entitled "Fiber optic sensor with an optical modulator having a permanent magnet for the detection of the movement or position of a magnetic component;" U.S. Pat. No. 5,285,407 issued to inventors Gale et al. on Feb. 8, 1994 and entitled "Memory circuit for spatial light modulator;" U.S. Pat. No. 5,867,302 issued to inventor Fleming on Feb. 2, 1999 and entitled "Bistable microelectromechanical actuator;" U.S. Pat. No. 6,178,284 issued to inventors Bergmann et al. on Jan. 23, 2001 and entitled "Variable single-mode attenuators by spatial interference;" U.S. Pat. No. 6,323,982 issued to inventor Hornbeck on Nov. 27, 2001 and entitled "Yield superstructure for digital micromirror device;" and U.S. Pat. No. 6,345,059 issued to inventor Flanders on Feb. 5, 2002 and entitled "Short cavity tunable laser with mode position compensation." All of the foregoing patents are hereby expressly incorporated by reference as if fully set forth in their entirety herein.

Some examples of electrostatically actuated membranes and methods of actuating electrostatic membranes, features of which may possibly be used or adapted for use in at least one possible embodiment may be found in the following U.S. Pat. No. 5,500,761 issued to inventors Goossen et al. on Mar. 19, 1996 and entitled "Micromechanical modulator;" U.S. Pat. No. 5,654,819 issued to Inventors Goossen et al. on Aug. 5, 1997 and entitled "Micromechanical modulator;" U.S. Pat. No. 5,991,066 issued to inventors Robinson et al. on Nov. 23, 1999 and entitled "Membrane-actuated charge controlled mirror;" U.S. Pat. No. 5,170,283 issued to inventors O'Brien et al. on Dec. 8, 1992 and entitled "Silicon spatial light modulator;" U.S. Pat. No. 6,031,657 issued to inventors Robinson et al. on Feb. 29, 2000 and entitled "Membrane-actuated charge controlled mirror (CCM) projection display;" U.S. Pat. No. 6,108,121 issued to inventors Mansell et al. on Aug. 22, 2000 and entitled "Micromachined high reflectance deformable mirror;" U.S. Pat. No. 6,168,395 issued to inventors Quenzer et al. on Jan. 2, 2001 and entitled "Bistable microactuator with coupled membranes;" and U.S. Pat. No. 6,178,033 issued to inventors Ford et al. on Jan. 23, 2001 and entitled "Micromechanical membrane tilt-mirror switch." All of the foregoing patents are hereby expressly incorporated by reference as if fully set forth in their entirety herein.

Some examples of piezoelectric actuated membranes and methods of actuating piezoelectric membranes, features of which may possibly be used or adapted for use in at least one possible embodiment may be found in the following U.S. Pat. No. 4,160,184 issued to inventor Ljung on Jul. 3, 1979 and entitled "Piezoelectric actuator for a ring laser;" U.S. Pat. No. 4,639,630 issued to inventors Rodloff et al. on Jan. 27, 1987 and entitled "Piezoceramic servo-drive for producing translational motion, especially for application to ring laser mirrors;" U.S. Pat. No. 4,924,131 issued to inventors Nakayama et al. on May 8, 1990 and entitled "Piezo-electric acceleration sensor;" U.S. Pat. No. 5,049,775 issued to inventor Smits on Sep. 17, 1991 and entitled "Integrated micromechanical piezoelectric motor;" U.S. Pat. No. 5,421,335 issued to inventor Wild on Jun. 6, 1995 and entitled "Intrinsically collimated ultrasonic transducer;" U.S. Pat. No. 5,892,314 issued to inventors Sager et al. on Apr. 6, 1999 and entitled "Piezoelectric circuit;" and U.S. Pat. No. 6,184,609 issued to inventors Johansson et al. on Feb. 6, 2001 and entitled "Piezoelectric actuator or motor, method therefor and method for fabrication thereof." All of the foregoing patents are hereby expressly incorporated by reference as if fully set forth in their entirety herein.

Some examples of bimorph actuated membranes and methods of actuating bimorph membranes, features of which may possibly be used or adapted for use in at least one possible embodiment may be found in the following U.S. Pat. No. 4,383,763 issued to inventors Hutchings et al. on May 17, 1983 and entitled "Controllable mirrors;" U.S. Pat. No. 4,844,577 issued to inventors Ninnis et al. on Jul. 4, 1989 and entitled "Bimorph electro optic light modulator;" U.S. Pat. No. 5,026,977 issued to inventor Hubbard, Jr. and entitled "Wavefront sensing and correction with deformable mirrors;" U.S. Pat. No. 5,159,498 issued to inventor Hubbard, Jr. on Oct. 27, 1992 and entitled "Active mirror assembly;" U.S. Pat. No. 5,903,380 issued to inventors Motamedi et al. on May 11, 1999 and entitled "Micro-electromechanical (MEM) optical resonator and method;" U.S. Pat. No. 6,108,175 issued to inventors Hawwa et al. on Aug. 22, 2000 and entitled "Bimorph piezoelectric microactuator head and flexure assembly;" and U.S. Pat. No. 6,275,320 issued to inventors Dhuler et al. on Aug. 14, 2001 and entitled "MEMS variable optical-attenuator." All of the foregoing patents are hereby expressly incorporated by reference as if fully set forth in their entirety herein.

Some examples of digital image editing, features of which may possibly be used or adapted for use in at least one possible embodiment may be found in the following U.S. Pat. No. 5,481,353 issued to inventors Hicks et al. on Jan. 2, 1996 and entitled "Apparatus for producing variable feature presentation sets;" U.S. Pat. No. 5,659,639 issued to inventors Mahoney et al. on Aug. 19, 1997 and entitled "Analyzing an image showing editing marks to obtain category of editing operation;" U.S. Pat. No. 5,815,645 issued to inventors Fredlund et al. on Sep. 29, 1998 and entitled "Method of combining two digital images;" U.S. Pat. No. 5,867,282 issued to inventors Fredlund et al. on Feb. 2, 1999 and entitled "Method of combining two digitally generated images wherein one is customized in view of the other;" U.S. Pat. No. 5,880,740 issued to inventors Halliday et al. on Mar. 9, 1999 and entitled "System for manipulating graphical composite image composed of elements selected by user from sequentially displayed members of stored image sets;" U.S. Pat. No. 5,936,615 issued to inventor Waters on Aug. 10, 1999 and entitled "Image-based touchscreen;" U.S. Pat. No. 6,075,542 issued to inventors Fredlund et al. on Jun. 13, 2000 and entitled "Method of combining two digital images;" U.S. Pat. No. 6,243,502 issued to inventors Christensen et al. on Jun. 5, 2001 and entitled "Image quality maintenance;" U.S. Pat. No. 6,254,239 issued to inventors Hibner, II et al. on Jul. 3, 2001 and entitled "Method and system for image visualization;" U.S. Pat. No. 6,282,362 issued to inventors Murphy et al. on Aug. 28, 2001 and entitled "Geographical position/image digital recording and display system;" U.S. Pat. No. 6,283,858 issued to inventors Hayes, Jr. et al. on Sep. 4, 2001 and entitled "Method for manipulating images;" U.S. Pat. No. 6,295,370 issued to inventor D'Hooge on Sep. 25, 2001 and entitled "Blocky picture template generator;" U.S. Pat. No. 6,285,372 issued to inventors Cowsar et al. on Sep. 4, 2001 and entitled "Multiresolution adaptive parameterization of surfaces;" U.S. Pat. No. 6,310,650 issued to inventors Johnson et al. on Oct. 30, 2001 and entitled "Method and apparatus for calibrating a tiled display;" and U.S. Pat. No. 6,317,141 issued to inventors Pavley et al. on Nov. 13, 2001 and entitled "Method and apparatus for editing heterogeneous media objects in a digital imaging device." All of the foregoing patents are hereby expressly incorporated by reference as if fully set forth in their entirety herein.

Some examples of image editing such as by morphing an image, features of which may possibly be used or adapted for use in at least one possible embodiment may be found in the following U.S. Pat. No. 5,245,562 issued to inventor Dettmer on Sep. 14, 1993 and entitled "Accumulating arithmetic memory integrated circuit;" U.S. Pat. No. 5,495,539 issued to inventor Sleverding on Feb. 27, 1996 and entitled "Image production using multidimensional selection of image transformations;" U.S. Pat. No. 5,623,587 issued to inventor Bulman on Apr. 22, 1997 entitled "Method and apparatus for producing an electronic image;" U.S. Pat. No. 5,745,668 issued to inventors Poggio et al. on Apr. 28, 1998 and entitled "Example-based image analysis and synthesis using pixel-wise correspondence;" U.S. Pat. No. 6,021,220 issued to inventor Anderholm on Feb. 1, 2000 and entitled "System and method for pattern recognition;" U.S. Pat. No. 6,055,335 issued to inventors Ida et al. on Apr. 25, 2000 and entitled "Method and apparatus for image representation and/or reorientation;" U.S. Pat. No. 6,097,853 issued to inventors Gu et al. on Aug. 1, 2000 and entitled "User definable windows for selecting image processing regions;" U.S. Pat. No. 6,111,582 issued to inventor Jenkins on Aug. 29, 2000 and entitled "System and method of image generation and encoding using primitive reprojection;" U.S. Pat. No. 6,215,516 issued to inventors Ma et al. on Apr. 10, 2001 and entitled "Method and apparatus for monoscopic to stereoscopic image conversion;" U.S. Pat. No. 6,266,165 issued to inventors Huang et al. on Jul. 24, 2001 and entitled "Method for morphing N-dimensional data using a scattered data transformation;" U.S. Pat. No. 6,282,362 issued to inventors Murphy et al. on Aug. 28, 2001 and entitled "Geographical position/image digital recording and display system;" U.S. Pat. No. 6,341,183 issued to inventor Goldberg on Jan. 22, 2002 and entitled "Graphical user interface for image acquisition and processing;" and U.S. Pat. No. 6,366,693 issued to inventors Silverbrook et al. on Apr. 2, 2002 and entitled "Digital image region detection method and apparatus." All of the foregoing patents are hereby expressly incorporated by reference as if fully set forth in their entirety herein.

Some examples of touch screens, features of which may possibly be used or adapted for use in at least one possible embodiment of the present invention may be found in the following U.S. Pat. No. 4,931,782 issued to inventor Jackson on Jun. 5, 1990 and entitled "Touch screen overlay with improved conductor durability;" U.S. Pat. No. 5,708,460 issued to inventors Young et al. on Jan. 13, 1998 and entitled "Touch screen;" U.S. Pat. No. 5,838,309 issued to inventors Robsky et al. on Nov. 17, 1998 and entitled "Self-tensioning membrane touch screen;" U.S. Pat. No. 6,016,140 issued to inventors Blouin et al. on Jan. 18, 2000 and entitled "Automatic touch screen calibration;" U.S. Pat. No. 6,072,475 issued to inventor van Ketwich on Jun. 6, 2000 and entitled "Touch screen;" U.S. Pat. No. 6,121,960 issued to inventors Carroll et al. on Sep. 19, 2000 and entitled "Touch screen systems and methods;" U.S. Pat. No. 6,211,856 issued to inventors Choi et al. on Apr. 3, 2001 and entitled "Graphical user interface touch screen with an auto zoom feature;" U.S. Pat. No. 6,278,443 issued to inventors Amro et al. on Aug. 21, 2001 and entitled "Touch screen with random finger placement and rolling on screen to control the movement of information on-screen;" and U.S. Pat. No. 6,346,955 issued to inventors Moon et al. on Feb. 12, 2002 and entitled "Method and apparatus for using a touch screen display on a portable intelligent communications device." All of the foregoing patents are hereby expressly incorporated by reference as if fully set forth in their entirety herein.

Some examples of touch pads and pointing or cursor control by way of touch pads, features of which may possibly be used or adapted for use in at least one possible embodiment may be found in the following U.S. Pat. No. 4,291,303 issued to inventors Cutler et al. on Sep. 22, 1981 and entitled "Touch pad and display tube circuitry;" U.S. Pat. No. 5,189,417 issued to inventors Caldwell et al. on Feb. 23, 1993 and entitled "Detection circuit for matrix touch pad;" U.S. Pat. No. 5,577,848 issued to inventor Bowen on Nov. 26, 1996 and entitled "Light controlled touch pad for cursor and selection control on a computer display;" U.S. Pat. No. 5,856,822 issued to inventors Du et al. on Jan. 5, 1999 and entitled "Touch-pad digital computer pointing;" and U.S. Pat. No. 5,956,019 issued to inventors Bang et al. on Sep. 21, 1999 and entitled "Touch-pad cursor control device." All of the foregoing patents are hereby expressly incorporated by reference as if fully set forth in their entirety herein.

Some examples of light pens or pointers and pointing or cursor control by way of light pens or pointers, features of which may possibly be used or adapted for use in at least one possible embodiment may be found in the following U.S. Pat. No. 4,275,395 issued to inventors Dewey et al. on Jun. 23, 1981 and entitled "Interactive projection display system;" U.S. Pat. No. 4,538,183 issued to inventors Kanno et al. on Aug. 27, 1985 and entitled "Image editing apparatus;" U.S. Pat. No. 5,151,688 issued to inventors Tanaka et al. on Sep. 29, 1992 and entitled "Input/output display panel with light pen;" U.S. Pat. No. 5,179,368 issued to inventors Lippincott on Jan. 12, 1993 and entitled "Method and apparatus for interfacing computer light pens;" U.S. Pat. No. 5,838,308 issued to inventors Knapp et al. on Nov. 17, 1998 and entitled "Optical touch input device;" U.S. Pat. No. 6,097,376 issued to inventors Rothschild et al. on Aug. 1, 2000 and entitled "Light pen system for use with a CRT scanning display;" and U.S. Pat. No. 6,337,918 issued to inventor Holehan on Jan. 8, 2002 and entitled "Computer system with integratable touchpad/security subsystem." All of the foregoing patents are hereby expressly incorporated by reference as if fully set forth in their entirety herein.

Some examples of image projectors and methods of image projection, features of which may possibly be used or adapted for use in at least one possible embodiment may be found in the following U.S. Pat. No. 4,048,653 issued to inventor Spooner on Sep. 13, 1977 and entitled "Visual display apparatus;" U.S. Pat. No. 4,352,664 issued to inventors Morrison et al. on Oct. 5, 1982 and entitled "Simulator having two independently servo-controlled projection systems;" U.S. Pat. No. 4,486,081 issued to inventor Coulter on Dec. 4, 1984 and entitled "Optical image projector;" U.S. Pat. No. 5,414,521 issued to inventor Ansley on May 9, 1995 and entitled "Dynamic distortion correction apparatus and method;" U.S. Pat. No. 5,506,597 issued to inventors Thompson et al. on Apr. 9, 1996 and entitled "Apparatus and method for image projection;" U.S. Pat. No. 5,828,485 issued to inventor Hewlett on Oct. 27, 1998 and entitled "Programmable light beam shape altering device using programmable mirrors;" U.S. Pat. No. 5,864,128 issued to inventor Plesko on Jan. 26, 1999 and entitled "Lens with variable focal length;" U.S. Pat. No. 5,911,490 issued to inventors Ishikawa et al. on Jun. 15, 1999 and entitled "Overhead projector;" U.S. Pat. No. 6,213,606 issued to inventors Holman et al. on Apr. 10, 2001 and entitled "Image projection system;" U.S. Pat. No. 6,243,207 issued to inventors Kawamura et al. on Jun. 5, 2001 and entitled "Display apparatus;" U.S. Pat. No. 6,297,814 issued to inventors Masuda et al. on Oct. 2, 2001 and entitled "Apparatus for and method of displaying image and computer-readable recording medium;" U.S. Pat. No. 6,364,490 issued to inventor Krause on Apr. 2, 2002 and entitled "Virtual image projection device;" U.S. Pat. No. 6,346,933 issued to inventor Lin on Feb. 12, 2002 and entitled "Interactive display presentation system;" and No. RE37,578 issued to inventor Gleckman on Mar. 12, 2002 and entitled "Image projection system." All of the foregoing patents are hereby expressly incorporated by reference as if fully set forth in their entirety herein.

Some examples of cathode ray tubes, features of which may possibly be used or adapted for use in at least one possible embodiment may be found in the following U.S. Pat. No. 4,032,968 issued to inventors Miyoshi et al. on Jun. 28, 1977 and entitled "Television image projecting system;" U.S. Pat. No. 4,611,241 issued to inventor Albin on Sep. 9, 1986 and entitled "Projecting television set up method and apparatus;" No. 4,717,248 issued to inventor LaRussa on Jan. 5, 1988 and entitled "Display system;" U.S. Pat. No. 5,608,579 issued to inventor Nomura on Mar. 4, 1997 and entitled "Projection TV set apparatus;" U.S. Pat. No. 5,982,458 issued to inventors Kishi et al. on Nov. 9, 1999 and entitled "Convergence correction circuit and three tube type projector having the same;" U.S. Pat. No. 6,061,038 issued to inventor Washburn on May 9, 2000 and entitled "Multi-deflection CRT display;" and U.S. Pat. No. 6,342,757 issued to inventors Shin et al. on Jan. 29, 2002 and entitled "Cathode ray tube for multimedia." All of the foregoing patents are hereby expressly incorporated by reference as if fully set forth in their entirety herein.

Some examples of laser treatment of vision defects, features of which may possibly be used or adapted for use in at least one possible embodiment may be found in the following U.S. Pat. No. 4,846,172 issued to inventor Berlin on Jul. 11, 1989 and entitled "Laser-delivery eye-treatment method;" U.S. Pat. No. 4,941,093 issued to inventors Marshall et al. on Jul. 10, 1990 and entitled "Surface erosion using lasers;" U.S. Pat. No. 5,141,506 issued to inventor York on Aug. 25, 1992 and entitled "Systems and methods for creating substrate surfaces by photoablation;" U.S. Pat. No. 5,277,911 issued to inventors Vlegas et al. on Jan. 11, 1994 and entitled "Ablatable mask of polyoxyalkylene polymer and ionic polysaccharide gel for laser reprofiling of the cornea;" U.S. Pat. No. 5,376,086 issued to inventors Khoobehi et al. on Dec. 27, 1994 and entitled "Laser surgical method of sculpting a patient's cornea and associated intermediate controlling mask;" U.S. Pat. No. 5,461,212 issued to inventors Seiler et al. on Oct. 24, 1995 and entitled "Astigmatic laser ablation of surfaces;" U.S. Pat. No. 5,490,849 issued to inventor Smith on Feb. 13, 1996 and entitled "Uniform-radiation caustic surface for photoablation;" U.S. Pat. No. 5,502,518 issued to inventor Lieberman on Mar. 26, 1996 and entitled "Asymmetric aspheric contact lens;" U.S. Pat. No. 5,891,132 issued to inventor Hohla on Apr. 6, 1999 and entitled "Distributed excimer laser surgery system;" U.S. Pat. No. 5,941,874 issued to inventor Hohla on Aug. 24, 1999 and entitled "Simulating a laser treatment on the eye by pretreating a contact lens;" U.S. Pat. No. 5,968,383 issued to inventors Yamazaki et al. on Oct. 19, 1999 and entitled "Laser processing apparatus;" U.S. Pat. No. 6,139,542 issued to inventor Hohla on Oct. 13, 2000 and entitled "Distributed excimer laser surgery system;" U.S. Pat. No. 6,149,609 issued to inventors Lieberman et al. on Nov. 21, 2000 and entitled "Method and apparatus for improving vision;" and U.S. Pat. No. 6,251,103 issued to inventor Berlin on Jun. 26, 2001 and entitled "Photoablative laser eye-treatment method." All of the foregoing patents are hereby expressly incorporated by reference as if fully set forth in their entirety herein.

Some examples of wavefront modulators, features of which may possibly be used or adapted for use in at least one possible embodiment may be found in the following U.S. Pat. No. 4,118,685 issued to inventor Simpson on Oct. 3, 1978 and entitled "Holographic signature processor;" U.S. Pat. No. 4,248,504 issued to inventors Albertinetti et al. on Feb. 3, 1981 and entitled "Piezoelectric wavefront modulator;" U.S. Pat. No. 4,257,686 issued to inventors Albertinetti et al. on Mar. 24, 1981 and entitled "Multiple layer piezoelectric wavefront modulator;" U.S. Pat. No. 4,280,756 issued to inventor Albertinetti on Jul. 28, 1981 and entitled "Piezoelectric bi-morph mirror actuator;" U.S. Pat. No. 5,247,222 issued to inventor Engle on Sep. 21, 1993 and entitled "Constrained shear mode modulator;" U.S. Pat. No. 5,281,887 issued to inventor Engle on Jan. 25, 1994 and entitled "Two independent spatial variable degree of freedom wavefront modulator;" U.S. Pat. No. 6,038,068 issued to inventors Takeshi et al. on Mar. 14, 2000 and entitled "Aberration correction system and astronomical telescope having the same;" U.S. Pat. No. 6,323,984 issued to inventor Trisnadi on Nov. 27, 2001 and entitled "Method and apparatus for reducing laser speckle;" and U.S. Pat. No. 6,344,640 issued to inventor Rhoads on Feb. 5, 2002 and entitled "Method for wide field distortion-compensated imaging." All of the foregoing patents are hereby expressly incorporated by reference as if fully set forth in their entirety herein.

Some examples of light emitting diode elements (LED) and LED displays, features of which may possibly be used or adapted for use in at least one possible embodiment may be found in the following U.S. Pat. No. 4,734,734 issued to inventor Yano on Mar. 29, 1988 and entitled "Image forming apparatus and erasure illumination device therefor;" U.S. Pat. No. 5,029,245 issued to inventors Keränen et al. on Jul. 2, 1991 and entitled "Procedure for controlling a radiation source and controllable radiation source;" U.S. Pat. No. 5,510,633 issued to inventors Orlowski et al. on Apr. 23, 1996 and entitled "Porous silicon light emitting diode arrays and method of fabrication;" U.S. Pat. No. 5,523,591 issued to inventors Fleming et al. on Jun. 4, 1996 and entitled "Assembly of LED array and lens with engineered light output profile and method for making the assembly;" U.S. Pat. No. 5,638,052 issued to Inventors Furuya et al. on Jun. 10, 1997 and entitled "LED matrix display with LED control switches adjacent to each LED;" U.S. Pat. No. 5,656,847 issued to inventors Okazaki et al. on Aug. 12, 1997 and entitled "LED lamp arrangement and LED matrix display;" U.S. Pat. No. 6,014,120 issued to inventors Chiu et al. on Jan. 11, 2000 and entitled "LED display controller and method of operation;" U.S. Pat. No. 6,104,437 issued to inventors Taira et al. on Aug. 15, 2000 and entitled "Display signal processing device having controllable LED display;" U.S. Pat. No. 6,243,020 issued to inventors Lam et al. on Jun. 5, 2001 and entitled "Method and apparatus for programmably driving and LED display;" U.S. Pat. No. 6,258,699 issued to inventors Chang et al. on Jul. 10, 2001 and entitled "Light emitting diode with a permanent substrate of transparent glass or quartz and the method for manufacturing the same;" U.S. Pat. No. 6,307,527 issued to inventors Youngquist et al. on Oct. 23, 2001 and entitled "LED display assembly;" and U.S. Pat. No. 6,348,905 issued to inventor Wong on Feb. 19, 2002 and entitled "LED display apparatus." All of the foregoing patents are hereby expressly incorporated by reference as if fully set forth in their entirety herein.

Some examples of liquid crystal display elements (LCD) and LCD displays, features of which may possibly be used or adapted for use in at least one possible embodiment may be found in the following U.S. Pat. No. 5,592,193 issued to inventor Chen on Jan. 7, 1997 and entitled "Backlighting arrangement for LCD display panel;" U.S. Pat. No. 5,648,860 issued to inventors Ooi et al. on Jul. 15, 1997 and entitled "Projection type color liquid crystal optical apparatus;" U.S. Pat. No. 5,682,520 issued to inventors Fang et al. on Oct. 28, 1997 and entitled "Array processor for morphological image processing;" U.S. Pat. No. 5,754,260 issued to inventors Ooi et al. on May 19, 1998 and entitled "Projection type color liquid crystal optical apparatus;" U.S. Pat. No. 6,007,927 issued to inventors Nishikawa et al. on Dec. 28, 1999 and entitled "Organic dispersion-type electroluminescence element having reflective insulating layer eliminating bad effects of impurities from inorganic high dielectric powder;" U.S. Pat. No. 6,081,420 issued to inventors Kim et al. on Jun. 27, 2000 and entitled "LCD display apparatus;" U.S. Pat. No. 6,158,124 issued to inventors Matsuoka et al. on Jan. 2, 2001 and entitled "Image receiving monitor using LCD;" U.S. Pat. No. 6,163,349 issued to inventors Nakanishi et al. on Dec. 19, 2000 and entitled "Projection-type color liquid crystal display device having non overlapping pixel images;" U.S. Pat. No. 6,211,852 issued to inventors Oono et al. on Apr. 3, 2001 and entitled "Liquid crystal display device;" U.S. Pat. No. 6,226,061 issued to inventor Tagusa on May 1, 2002 and entitled "Liquid crystal display device having phase different plates;" U.S. Pat. No. 6,273,567 issued to inventors Conner et al. on Aug. 14, 2001 and entitled "Compact multi-path projector;" U.S. Pat. No. 6,282,029 issued to inventors Ma et al. on Aug. 28, 2001 and entitled "Compact display system;" U.S. Pat. No. 6,300,990 issued to inventors Yamaguchi et al. on Oct. 9, 2001 and entitled "Reflective LCD device with low visual angle dependency and high contrast;" U.S. Pat. No. 6,320,221 issued to inventors Ohoi et al. on Nov. 20, 2001 and entitled "TFT-LCD having a vertical thin film transistor;" and U.S. Pat. No. 6,320,226 issued to inventors Gu et al. on Nov. 20, 2001 and entitled "LCD with increased pixel opening sizes." All of the foregoing patents are hereby expressly incorporated by reference as if fully set forth in their entirety herein.

Some examples of the utilization of a Taylor polynomial, features of which may possibly be used or adapted for use in at least one possible embodiment may be found in the following U.S. Pat. No. 5,410,643 issued to inventors Youndin et al on Apr. 25, 1995 and entitled "Compressed image production storage transmission and processing;" U.S. Pat. No. 5,604,691 issued to inventors Dworkin et al. on Feb. 18, 1997 and entitled "Logarithm/inverse-logarithm converter utilizing a truncated Taylor series and method of use;" and U.S. Pat. No. 5,960,118 issued to inventors Briskin et al on Sep. 28, 1999 and entitled "Method for 2D and 3D images capturing, representation, processing and compression." All of the foregoing patents are hereby expressly incorporated by reference as if fully set forth in their entirety herein.

Some examples of utilization of a Zernike polynomial, features of which may possibly be used or adapted for use in at least one possible embodiment may be found in the following U.S. Pat. No. 6,201,646 issued to inventors Togino et al. on Mar. 13, 2001 and entitled "Image-forming optical system and viewing optical system;" U.S. Pat. No. 6,249,391 issued to inventors Hayakawa et al on Jun. 19, 2001 and entitled "Image-forming optical system;" U.S. Pat. No. 6,257,723 issued to inventors Sarver et al on Jul. 10, 2001 and entitled "Device and method for mapping the topography of an eye using elevation measurements in combination with slope measurements;" U.S. Pat. No. 6,299,311 issued to inventors Williams et al. on Oct. 9, 2001 and entitled "Rapid, automatic measurement of the eye's wave aberrations;" U.S. Pat. No. 6,313,951 issued to inventors Manhart et al. on Nov. 6, 2001 and entitled "Optical system with Zernike-shaped corrector;" U.S. Pat. No. 6,341,183 issued to inventor Goldberg on Jan. 22, 2002 and entitled "Graphical user interface for image acquisition and processing;" and U.S. Pat. No. 6,342,871 issued to inventor Takeyama on Jan. 29, 2002 and entitled "Image display apparatus." All of the foregoing patents are hereby expressly incorporated by reference as if fully set forth in their entirety herein.

The details in the patents, patent applications and publications may be considered to be incorporable, at Applicants' option, into the claims during prosecution as further limitations in the claims to patentably distinguish any amended claims from any applied prior art.

Some examples of eye testing and measuring devices and components or methods thereof which may possibly be used or adapted for use in at least one possible embodiment may be found in the following U.S. Pat. No. 6,948,818, entitled "Method and apparatus for improving vision and the resolution of retinal images"; U.S. Pat. No. 6,827,444, entitled "Rapid, automatic measurement of the eye's wave aberration"; U.S. Pat. No. 6,511,180, entitled "Determination of ocular refraction from wavefront aberration data and design of optimum customized correction"; U.S. Pat. No. 6,394,999, entitled "Laser eye surgery system using wavefront sensor analysis to control digital micromirror device (DMD) mirror patterns"; U.S. Pat. No. 6,379,005, entitled "Method and apparatus for improving vision and the resolution of retinal"; U.S. Pat. No. 6,338,559, entitled "Apparatus and method for improving vision and retinal imaging"; U.S. Pat. No. 6,299,311, entitled "Rapid, automatic measurement of the eye's wave aberration"; U.S. Pat. No. 6,264,328, entitled "Wavefront sensor with off-axis illumination"; U.S. Pat. No. 6,199,986, entitled "Rapid, automatic measurement of the eye's wave aberration"; U.S. Pat. No. 6,095,651, entitled "Method and apparatus for improving vision and the resolution of retinal images"; U.S. Pat. No. 5,949,521, entitled "Method and apparatus for improving vision and the resolution of retinal images"; and U.S. Pat. No. 5,777,719, entitled "Method and apparatus for improving vision and the resolution of retinal images.

One feature of at least one possible embodiment resides broadly in a method for determining vision defects and for collecting data for correcting vision defects of the eye 10 by interaction of a patient with an examiner, said method comprising: projecting 61 an image 45 into the eye 10 of the patient with an adaptive optical system 30; said adaptive optical system 30 comprising at least one adaptive optical element 31; said at least one adaptive optical element 31 being configured to have its optical characteristics changed by an electrical signal, in an attempt to minimize distortions of the image as perceived in the eye 10 and the brain of the patient; determining 62 the presence of distortions of the image as perceived by in the eye 10 and the brain of the patient by interaction of the patient with the examiner; providing an electronic control system 50; said electronic control system 50 being configured to control the optical characteristics of said at least one adaptive optical element 31 through outputting of an electrical signal; modifying 64 the optical characteristics of said at least one adaptive optical element 31 through outputting of an electrical signal of said electronic control system 50 and obtaining a modified image of the image in the eye 10 of the patient, in an attempt to correct for the distortions of the image as perceived in the eye 10 and the brain of the patient; evaluating 66 said modified image by interaction of the patient with the examiner; repeating said modifying step 64 and said evaluating step 66 and obtaining a modified image having minimized distortions as perceived in the eye 10 and the brain of the patient; determining the optical characteristics of said at least one adaptive optical element 31, as modified, resulting from said modified image having minimized distortions as perceived in the eye 10 and the brain of the patient; and computing 79 vision correcting data 55 for the eye 10 being examined, from said optical characteristics of said at least one adaptive optical element 31, as modified, resulting from said modified image having minimized distortions as perceived in the eye 10 and the brain of the patient.

Another feature of at least one possible embodiment resides broadly in the method wherein: said adaptive optical system 30 comprises a micromirror device 30 operatively connected to said electronic control system 50; said micromirror device comprising a plurality of micromirrors 31; said micromirrors 31 comprising arrangements configured to respond to output signals from said electronic control system 50; and said micromirrors 31 being configured to change the optical characteristics in response to output signals from said electronic control system 50; said micromirrors 31 being configured to generate signals indicative of the modified optical characteristics of said micromirrors 31 resulting from said modified image having minimized distortions as perceived in the eye 10 and the brain of the patient; said method comprising: providing electrical signals from said electronic control system 50 to said micromirrors 31 to change the optical characteristics of said micromirrors 31; and providing signals from said micromirrors 31 indicative of the modified optical characteristics of said micromirrors 31 to an arrangement 50 for computing vision correcting data 55 for the eye 10 being examined.

Yet another feature of at least one possible embodiment resides broadly in the method wherein: said micromirrors 31 are configured to be moveable to and stoppable in a plurality of positions between a first extreme position and a second extreme position opposite from said first extreme position; said method comprising: moving said micromirrors 31 from a first position corresponding to an image projected into the eye 10 of the patient to a second position corresponding to a modified image having minimized distortions as perceived in the eye 10 and the brain of the patient.

Still another feature of at least one possible embodiment resides broadly in the method wherein: said adaptive optical system 30 is configured substantially as a segment of a sphere; said method comprising: projecting an image onto said optical system 30 configured substantially as a segment of a sphere; and reflecting an image from said adaptive optical system 30 substantially configured as a segment of a sphere, into the eye 10 of the patient.

A further feature of at least one possible embodiment resides broadly in the method wherein: each micromirror 31 is configured to be moved by a membrane 34; said membrane 34 being configured to be actuated by a force of one: an electrostatic arrangement, a piezo-electric arrangement, and a bimorph membrane arrangement; said method comprising: moving said membrane 34 by one of: an electrostatic force, a piezo-electric force, and a bimorph membrane force.

Another feature of at least one possible embodiment resides broadly in the method comprising: determining aberrations of the eye 10 of the patient with an aberrometer device 80 configured to measure aberrations of the eye 10 of the patient; obtaining data 85 indicative of the aberrations of the eye 10 of the patient; and correlating said data 85 from said aberrometer 80 indicative of the aberrations of the eye 10 of the patient, with said vision correcting data 55 computed from said at least one adaptive optical element 31, as modified.

Yet another feature of at least one possible embodiment resides broadly in the method wherein: said aberrometer device 80 comprises a Shack-Hartmann sensor.

Still another feature of at least one possible embodiment resides broadly in the method wherein: said electronic control system 50 comprises a computer configured to compute vision correcting data 55 using a Taylor polynomial and/or a Zernike polynomial; said method comprising: computing 79 vision correcting data 55, using a Taylor polynomial and/or a Zernike polynomial, on the basis of said data 85 from said aberrometer 80 indicative of the aberrations of the eye 10 of the patient, and said vision correcting data 55 computed from said at least one adaptive optical element 31, as modified; and applying corrective treatment 60 to the eye 10 being examined.

A further feature of at least one possible embodiment resides broadly in the method for determining vision defects and for collecting data for correcting vision defects of the eye 10 by interaction with a patient, said method comprising: forming 61 an image in the eye 10 of the patient with an optical system 30; said optical system 30 being configured to have its optical characteristics changed by at least one signal, in an attempt to minimize distortions of the image as perceived in the eye 10 and the brain of the patient; determining the presence of distortions of the image as perceived in the eye 10 and the brain of the patient by interaction with the patient; providing an electronic control system 50 being configured to control the optical characteristics of said optical system 30 through outputting of at least one signal; modifying 64, at least once, the optical characteristics of said optical system 30 through outputting of at least one signal of said electronic control system 50 and obtaining a modified image of the image in the eye 10 of the patient, in an attempt to correct for the distortions of the image as perceived in the eye 10 and the brain of the patient by interaction with the patient; determining 70 the optical characteristics of said optical system 30, as modified, resulting from said modified image of the image in the eye 10 of the patient having minimized distortions as perceived in the eye 10 and the brain of the patient; and computing 79 vision correcting data 55 for the eye being examined, from at least one signal indicating said modified optical characteristics of said optical system 30.

Another feature of at least one possible embodiment resides broadly in the method wherein: said optical system 30 comprises a micromirror device 30 operatively connected to said electronic control system 50; said micromirror device 30 comprises a plurality of micromirrors 31; said micromirrors 31 comprise arrangements 36 configured to respond to output signals from said electronic control system 50; and said micromirrors 31 being configured to change the optical characteristics in response to output signals from said electronic control system 50; said micromirrors 31 are configured to generate signals indicative of the modified optical characteristics of said micromirrors 31 resulting from said modified image of the image in the eye 10 of the patient having minimized distortions as perceived by the patient; said method comprising: providing at least one electrical signal from said electronic control system 50 to said micromirrors 31 to change the optical characteristics of said micromirror device 30; and providing at least one signal from said micromirrors 31 indicative of the modified optical characteristics of said micromirrors 31 to an arrangement 50 for computing vision correcting data 55 for the eye 10 being examined.

Yet another feature of at least one possible embodiment resides broadly in the method wherein: said micromirrors 31 are configured to be moveable to and stoppable in a plurality of positions between a first extreme position and a second extreme position opposite from said first extreme position; said method comprising: moving said micromirrors 31 from a first position corresponding to an image formed in the eye 10 of the patient to a second position corresponding to a modified image formed in the eye 10 of the patient having minimized distortions as perceived in the eye 10 and the brain of the patient.

Still another feature of at least one possible embodiment resides broadly in the method wherein: said optical system 30 is configured substantially as a segment of a sphere; said method comprising:
projecting an image onto said optical system 30 configured substantially as a segment of a sphere; and
reflecting an image from said optical system 30 configured substantially as a segment of a sphere, into the eye 10 of the patient.

A further feature of at least one possible embodiment resides broadly in the method comprising one of: (a.) each micromirror 31 is configured to be moved by a membrane 34; said membrane 34 being configured to be actuated by a force of one of: an electrostatic arrangement, a piezo-electric arrangement, and a bimorph membrane arrangement; said method further comprising: moving said membrane 34 by one of: an electrostatic force, a piezo-electric force, and a bimorph membrane force; (b.) determining aberrations of the eye 10 of the patient with an aberrometer device 80 configured to measure aberrations of the eye 10 of the patient; obtaining data 85 indicative of the aberrations of the eye 10 of the patient; and correlating said data 85 from said aberrometer 80 indicative of the aberrations of the eye 10 of the patient, with said vision correcting data 55 computed from said optical system 30, as modified, resulting from said modified image formed in the eye 10 of the patient having minimized distortions as perceived in the eye 10 and the brain of the patient; (c.) said aberrometer device 80 comprises a Shack-Hartmann sensor; and (d.) said electronic control system 50 comprises a computer configured to compute vision correcting data 55 using a Taylor polynomial and/or a Zernike polynomial; said method further comprising: computing 79 vision correcting data 55, using a Taylor polynomial and/or a Zernike polynomial, on the basis of said data 85 from said aberrometer 80 indicative of the aberrations of the eye 10 of the patient, and said vision correcting data 55 computed for the eye 10 being examined from said optical system 30, as modified; and applying corrective treatment 60 to the eye 10 being examined.

Another feature of at least one possible embodiment resides broadly in the method comprising all of: (a.) each micromirror 31 is configured to be moved by a membrane 34; said membrane 34 being configured to be actuated by a force of one of: an electrostatic arrangement, a piezo-electric arrangement, and a bimorph membrane arrangement; said method further comprising: moving said membrane 34 by one of: an electrostatic force, a piezo-electric force, and a bimorph membrane force; (b.) determining aberrations of the eye 10 of the patient with an aberrometer device 80 configured to measure aberrations of the eye 10 of the patient; obtaining data 85 indicative of the aberrations of the eye 10 of the patient; and correlating said data 85 from said aberrometer 80 indicative of the aberrations of the eye 10 of the patient, with said vision correcting data 55 computed from said optical system 30, as modified; said aberrometer device 80 comprises a Shack-Hartmann sensor; and (d.) said electronic control system 50 comprises a computer configured to compute 79 vision correcting data 55 using a Taylor polynomial and/or a Zernike polynomial; said method further comprising: computing 79 vision correcting data 55, using a Taylor polynomial and/or a Zernike polynomial, on the basis of said data 85 from said aberrometer 80 indicative of the aberrations of the eye 10 of the patient, and said vision correcting data 55 computed from said optical system 30, as modified; and applying corrective treatment 60 to the eye 10 being examined.

Yet another feature of at least one possible embodiment resides broadly in the apparatus for determining vision defects and for collecting data for correcting vision defects of the eye by interaction between a patient and an examiner, said apparatus comprising: an adaptive optical system 30 configured to form an image in the eye 10 of the patient; said adaptive optical system 30 being configured to have its optical characteristics changed by at least one signal, in an attempt to minimize distortions of the image as perceived in the eye 10 and the brain of the patient; an electronic control system 50 operatively connected to said adaptive optical system 30; said electronic control system 50 comprising an arrangement configured to modify, at least once, the optical characteristics of said adaptive optical system 30, and being configured to output at least one signal to obtain a modified image, in an attempt to correct for the distortions of the image as perceived in the eye 10 and the brain of the patient through interaction with the patient; an arrangement configured to determine the optical characteristics of said adaptive optical system, as modified, resulting from said modified image formed in the eye 10 of the patient having minimized distortions as perceived in the eye 10 and the brain of the patient; and apparatus 50 configured to compute vision correcting data 55 for the eye 10 being examined, from at least one signal indicating said modified optical characteristics of said adaptive optical system 30.

Still another feature of at least one possible embodiment resides broadly in the apparatus wherein: said adaptive optical system 30 comprises a micromirror device operatively connected to said electronic control system 50; said micromirror device comprising a plurality of micromirrors 31; said micromirrors 31 are configured to individually change optical characteristics in response to output signals from said electronic control system 50 independently of an adjacent micromirror 31; said micromirrors 31 are configured to generate signals indicative of the modified optical characteristics of said micromirrors 31 resulting from said modified image formed in the eye 10 of the patient having minimized distortions as perceived in the eye 10 and the brain of the patient.

A further feature of at least one possible embodiment resides broadly in the apparatus wherein: said micromirrors 31 are configured to be moveable to and stoppable in a plurality of positions between a first extreme position and a second extreme position opposite from said first extreme position.

Another feature of at least one possible embodiment resides broadly in the apparatus wherein: said adaptive optical system 30 is configured substantially as a segment of a sphere.

Yet another feature of at least one possible embodiment resides broadly in the apparatus comprising one of: (a.) each micromirror 31 is configured to be moved by a membrane 34; said membrane 34 being configured to be actuated by a force of one of: an electrostatic arrangement, a piezo-electric arrangement, and a bimorph membrane arrangement; (b.) an aberrometer device 80 configured to measure aberrations of the eye 10 of the patient; (c.) an aberrometer device 80 comprising a Shack-Hartmann sensor; and (d.) said electronic control system 50 comprises a computer configured to compute vision correcting data 55 using a Taylor polynomial and/or a Zernike polynomial on the basis of data 85 from said aberrometer 80 indicative of the aberrations of the eye 10 of the patient, and vision correcting data 55 computed from said adaptive optical system 30, as modified.

Still another feature of at least one possible embodiment resides broadly in the apparatus comprising all of: (a.) each micromirror 31 is configured to be moved by a membrane 34; said membrane 34 being configured to be actuated by a force of one of: an electrostatic arrangement, a piezo-electric arrangement, and a bimorph membrane arrangement; (b.) an aberrometer device 80 configured to measure aberrations of the eye 10 of the patient; (c.) said aberrometer device 80 comprises a Shack-Hartmann sensor; and (d.) said electronic control system 50 comprises a computer configured to compute vision correcting data 55 using a Taylor polynomial and/or a Zernike polynomial on the basis of data 85 from said aberrometer 80 indicative of the aberrations of the eye 10 of the patient, and said vision correcting data 55 computed from said adaptive optical system 30, as modified.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents but also equivalent structures.

The invention as described hereinabove in the context of the embodiments is not to be taken as limited to all of the provided details thereof, since modifications and variations thereof may be made without departing from the spirit and scope of the invention.

At least partial list of reference numerals: 10 eye; 20 optical system; 30 adaptive optics; 31 mirror; 32 optical interface; 34 mechanical interface; 35 adaptive data; 36 addressing circuitry; 40 image projector; 45 test image; 50 control system; 51 first control system (adaptive optics); 52 second control system (computation of correction data); 55 correction data; 60 laser system; 80 aberrometer; 85 aberrations data.

What is claimed is:

1. An apparatus for determining defects of the retina of the eye by interaction between a patient and an examiner, said apparatus comprising:

an adaptive optical system configured to form an image in the eye of the patient;

said adaptive optical system being configured to have its optical characteristics changed by at least one signal, in an attempt to compensate distortions of the image due to aberrations of the eye and thus defining a first set of aberration data which correspond to the objective aberrations of the eye;

an electronic control system operatively connected to said adaptive optical system;

said electronic control system comprising an arrangement configured to modify, at least once, the optical characteristics of said adaptive optical system, and being configured to output at least one signal to obtain a modified image, in an attempt to correct for the distortions of the image as perceived by the patient through interaction with the patient in a subjective assessment thus defining a second set of aberration data; and an image sensor, being adapted to obtain the first image data and the second image data corresponding to first and second aberration data, the apparatus being adapted to compare the first set of data and the second set of data and determine the regions of the retina related to these sets of data in which these sets of data are different.

2. The apparatus according to claim 1, wherein the apparatus is configured to compare the first set of aberration data and the second set of a aberration data and to determine the regions of the retina related to these sets of data in which these sets of data are different.

3. The apparatus according to claim 2, wherein the image sensor comprises at least one of: a fundus camera, a fundus camera with an adaptive optic, a confocal laser scanner and an optical coherence tomograph.

4. The apparatus according to claim 3, further comprising a correction element comprising input elements.

5. The apparatus according to claim 4, being adapted to carry out a test for different colors comprising blue, red, and green to test the different cones of the macula on the retina.

6. The apparatus according to claim 5, further comprising a monitor to visualize the regions of the retina of the eye related to these sets of data in which these sets of data are different.

7. The apparatus according to claim 6, wherein a degree of difference between the two data sets is indicatable by a color.

8. The apparatus according to claim 1, wherein the image sensor comprises at least one of: a fundus camera, a fundus camera with an adaptive optic, a confocal laser scanner and an optical coherence tomograph.

9. The apparatus according to claim 1, further comprising a correction element comprising input elements.

10. The apparatus according to claim 1, being adapted to carry out the test for different colors comprising blue, red, and green to test the different cones of the macula on the retina.

11. The apparatus according to claim 1, further comprising a monitor to visualize the regions of the retina of the eye related to these sets of data in which these sets of data are different.

12. The apparatus according to claim 1, wherein a degree of difference between the two data sets is indicatable by a color.

13. A method for determining defects of the retina of the eye using a testing apparatus and by interaction between a patient and an examiner, said method comprising the steps of:
forming an image in the eye of the patient using an adaptive optical system;
changing, by at least one signal, the optical characteristics of said adaptive optical system to compensate for distortions of the image due to aberrations of the eye and thus defining a first set of aberration data which correspond to the objectively-detected aberrations of the eye;
evaluating said image by interaction of the patient with the examiner;
outputting at least one signal from an electronic control system operatively connected to said adaptive optical system and modifying, at least once, the optical characteristics of said adaptive optical system to obtain a modified image to correct for the distortions of the image as perceived by the patient through interaction with the patient in a subjective assessment thus defining a second set of aberration data;
obtaining the first image data and the second image data corresponding to first and second aberration data with an image sensor; and
comparing the first set of data and the second set of data and determining the regions of the retina related to these sets of data in which these sets of data are different.

14. The method according to claim 13, wherein said step of comparing the first and second sets of data comprises comparing the first set of aberration data and the second set of adaptive data and to determine the regions of the retina related to these sets of data in which these sets of data are different.

15. The method according to claim 14, wherein the image sensor comprises at least one of: a fundus camera, a fundus camera with an adaptive optic, a confocal laser scanner and an optical coherence tomograph.

16. The method according to claim 15, wherein the testing apparatus comprises a correction element comprising input elements.

17. The method according to claim 16, wherein:
said method further comprises the step of testing for different colors comprising blue, red, and green to test the different cones of the macula on the retina;
the testing apparatus comprises a monitor to visualize the regions of the retina of the eye related to these sets of data in which these sets of data are different; and
a degree of difference between the two data sets is indicatable by a color.

18. A method for determining defects of the retina of the eye using a testing apparatus and by interaction between a patient and an examiner, said testing apparatus comprising:
an adaptive optical system configured to form an image in the eye of the patient;
said adaptive optical system being configured to have its optical characteristics changed by at least one signal, in an attempt to compensate distortions of the image due to aberrations of the eye and thus defining a first set of aberration data which correspond to the objective aberrations of the eye;
an electronic control system operatively connected to said adaptive optical system;
said electronic control system comprising an arrangement configured to modify, at least once, the optical characteristics of said adaptive optical system, and being configured to output at least one signal to obtain a modified image, in an attempt to correct for the distortions of the image as perceived by the patient through interaction with the patient in a subjective assessment thus defining a second set of aberration data; and
an image sensor, being adapted to obtain the first image data and the second image data corresponding to first and second aberration data, the apparatus being adapted to compare the first set of data and the second set of data and determine the regions of the retina related to these sets of data in which these sets of data are different;
and said method comprising the steps of:
forming an image in the eye of the patient using said adaptive optical system;
changing, by at least one signal, the optical characteristics of said adaptive optical system to compensate for distortions of the image due to aberrations of the eye and thus defining a first set of aberration data which correspond to the objectively-detected aberrations of the eye;
evaluating said modified image by interaction of the patient with the examiner;
outputting at least one signal from said electronic control system operatively connected to said adaptive optical system and modifying, at least once, the optical characteristics of said adaptive optical system to obtain a modified image to correct for the distortions of the image as perceived by the patient through interaction with the patient in a subjective assessment thus defining a second set of aberration data;
obtaining the first image data and the second image data corresponding to first and second aberration data with said image sensor; and
comparing the first set of data and the second set of data and determining the regions of the retina related to these sets of data in which these sets of data are different.

19. The method according to claim 18, wherein said step of comparing the first and second sets of data comprises comparing the first set of aberration data and the second set of adaptive data and to determine the regions of the retina related to these sets of data in which these sets of data are different.

20. The method according to claim 19, wherein:
the image sensor comprises at least one of: a fundus camera, a fundus camera with an adaptive optic, a confocal laser scanner and an optical coherence tomograph;
the testing apparatus comprises a correction element comprising input elements;
said method further comprises the step of testing for different colors comprising blue, red, and green to test the different cones of the macula on the retina;
the testing apparatus comprises a monitor to visualize the regions of the retina of the eye related to these sets of data in which these sets of data are different; and
a degree of difference between the two data sets is indicatable by a color.

* * * * *